United States Patent [19]
Summerton et al.

[11] Patent Number: 6,060,246
[45] Date of Patent: May 9, 2000

[54] REAGENT AND METHOD FOR ISOLATION AND DETECTION OF SELECTED NUCLEIC ACID SEQUENCES

[75] Inventors: James E. Summerton; Dwight D. Weller, both of Corvallis, Oreg.; John M. Wages, Jr., Pacifica, Calif.

[73] Assignee: AVI BioPharma, Inc., Corvallis, Oreg.

[21] Appl. No.: 08/969,813

[22] Filed: Nov. 13, 1997

Related U.S. Application Data

[60] Provisional application No. 60/030,963, Nov. 15, 1996.

[51] Int. Cl.[7] .............................. C12Q 1/68; C07H 21/02; C07H 21/04; C12N 15/00
[52] U.S. Cl. ........................... 435/6; 536/23.1; 536/24.3; 935/76; 935/77; 935/78
[58] Field of Search ............................... 435/6; 536/23.1, 536/24.3; 935/76, 77, 78

[56] References Cited

U.S. PATENT DOCUMENTS

| | | | |
|---|---|---|---|
| 5,075,430 | 12/1991 | Little | 536/27 |
| 5,142,047 | 8/1992 | Summerton et al. | 544/118 |
| 5,234,809 | 8/1993 | Boom et al. | 435/91 |
| 5,512,439 | 4/1996 | Hornes et al. | 435/6 |
| 5,539,082 | 7/1996 | Nielsen et al. | 530/300 |
| 5,629,158 | 5/1997 | Uhlen | 435/6 |

FOREIGN PATENT DOCUMENTS

| | | |
|---|---|---|
| WO90/06042 | 6/1990 | WIPO . |
| WO91/08307 | 6/1991 | WIPO . |

OTHER PUBLICATIONS

Elaissari, Abdelhamid, et al., "Adsorption and Desorption Studies of Polyadenylic Acid onto Positively Charged Latex Particles," Langmuir 11:1261–1267 (1995).

Kuribayashi–Ohta, Keiko, et al., "Application of oligo(dT)$_{30}$–latex for rapid purification of poly(A)$^+$ mRNA and for hybrid subtraction with the in situ reverse transcribed cDNA," Biochemica et Biophysica Acta 1156:204–212 (1993).

Lund, Vera, et al., "Assessment of methods for covalent binding of nucleic acids to magnetic beads, Dynabeads™ and the characteristics of the bound nucleic acids in hybridization reactions," Nuc. Acids, Res. 16(22):10861–10881 (1988).

Ørum, H., et al., "Sequence–Specific Purification fo Nucleic Acids by PNA–Controlled Hybrid Selection," BioTechniques 19(3): 472–480 (1995).

Wolf, Stanley F., et al., "Rapid hybridization kinetics of DNA attached to submicron latex particles," Nuc. Acids Res. 15(7):2911–2927 (1987).

*Primary Examiner*—W. Gary Jones
*Assistant Examiner*—Ethan Whisenant
*Attorney, Agent, or Firm*—LeeAnn Gorthey Dehlinger & Associates

[57] ABSTRACT

The invention relates to compositions and methods for rapidly detecting or isolating a target nucleic acid sequence in a polynucleotide-containing sample. The sample is exposed to a rapid pairing reagent, which contains a rapid capture component, effective to rapidly and non-selectively bind polynucleotides, and a target specific probe, effective to selectively bind the target nucleic acid sequence. Selectively disrupting the binding between the capture component and polynucleotides leaves only target sequence bound to the rapid pairing reagent.

18 Claims, 9 Drawing Sheets

B = adenine, cytosine, guanine, uracil

REAGENT AND METHOD FOR ISOLATION AND DETECTION OF SELECTED NUCLEIC ACID SEQUENCES

This application claims benefit of Provisional application Ser. No. 60/030,963 filed Nov. 15, 1996.

FIELD OF THE INVENTION

The present invention relates to compositions and methods for rapidly detecting or isolating a target nucleic acid sequence in a polynucleotide-containing sample.

REFERENCES

Chang et al., *Biopolymers* 13:1847 (1974).
Froehler et al., *Nucleic Acids Res.* 16:4831 (1988).
Gillespie and Spiegelman, *J. Mol. Biol.* 12:829 (1965).
Harris, in *POLY (ETHYLENE GLYCOL) CHEMISTRY: BIOTECHNICAL AND BIOMEDICAL APPLICATIONS* Plenum Press, NY, N.Y. (1992).
Kohne et al., *Biochemistry* 16:5329 (1977).
Miller et al., *J. American Chem. Soc.* 93:6657 (1971).
Miller et al., *Biochemistry* 20:1874 (1981).
Nielsen, P. E. et al., *Science* 254:1497–1500 (1991).
Stirchak, E. et al., *J. Organic Chem.* 52:4202 (1987).
Stirchak, E. et al., *Nucleic Acids Research* 17:6129 (1989).
Stirchak, E., U.S. Pat. No. 5,235,033 (1993).
Summerton, J. E. and Weller, D. W., U.S. Pat. No. 5,166,315 (1992).
Summerton, J. E. and Weller, D. W., U.S. Pat. No. 5,142,047 (1992).
Summerton, J. E. and Weller, D. W., U.S. Pat. No. 5,185,444 (1993).
Summerton, J. E. and Weller, D. W., U.S. Pat. No. 5,405,938 (1995).
Wetmur, *Biopolymers* 14:2517 (1975).

BACKGROUND OF THE INVENTION

Sequence-specific isolation and detection of selected polynucleotides in complex biological specimens is an important process in many fields, including medical diagnostics and drug research. In spite of recent advances, the process remains relatively slow, complex, and labor intensive. In a typical method (Gillespie and Spiegelman, 1965), single-stranded polynucleotides are fixed on a suitable surface, such as a nitrocellulose filter. A labeled sequence-specific probe is then added under annealing conditions, and, following a suitable annealing period (typically many hours), unpaired probe is washed away, and the surface is assessed for label. While this strategy has proven extremely valuable in a broad range of applications, it is quite slow and labor intensive, and affords relatively low signal to noise discrimination, particularly when the sequence to be detected is present at low concentrations, as is often the case with clinical specimens.

In various solution-based strategies, the sequence-specific pairing step is carried out in solution, followed by capture of the paired probe on a suitable surface. A number of methods have been developed to increase the speed of pairing between complementary sequences. These generally serve to increase the concentration of nucleic acids in the specimen, e.g. at a phenol/water interface (Kohne et al., 1977) or by including additives which physically exclude nucleic acids from a substantial volume of the solution (Wetmur 1975; Chang et al., 1974). This increased pairing rate, however, is generally accompanied by a significant increase in background signal.

Because of these limitations, such methods remain unsuited for many commercial applications. In particular, conventional sample preparation methods for amplification-based diagnostics, such as PCR, often isolate polymerase inhibitors, which are present in many clinical samples, along with the desired polynucleotides.

It is therefore desirable to provide a method of detecting or isolating target polynucleotides from complex samples which is both rapid and selective, allows detection of low levels of analyte, and requires a minimum of complex manipulations.

SUMMARY OF THE INVENTION

The present invention includes, in one aspect, a rapid pairing reagent for isolation or detection of a polynucleotide analyte molecule having a selected target base sequence in a polynucleotide-containing sample. The reagent includes a solid substrate to which is linked a capture component effective to non-selectively bind polynucleotide molecules in the sample. Also linked to the substrate is a target-specific probe which is effective to selectively bind the target base sequence. In accordance with the invention, the capture component is effective to release bound polynucleotides under conditions which do not disrupt the linkage, formed via the target-specific probe, between the substrate and the target sequence. In a preferred embodiment, the capture component and the target-specific probe are linked to the substrate in a relative proximity which allows concomitant binding of the analyte molecule to the capture component and to the target-specific probe.

The capture component may be an amine which has a pKa in the range of about 4.0 to about 8.0 and is effective to bind polynucleotides at a pH below its pKa and to release polynucleotides at a pH substantially above its pKa. This amine is preferably a polymeric amine, also referred to as an oligoamine.

In one embodiment, the capture component is linked to the substrate via a cleavable linkage. The cleavable linkage may be, for example, a disulfide, a vicinal diol, an ortho-nitrobenzyl ester, an ester, a peptide, or an oligosaccharide. A preferred capture component is a nucleic acid-binding polymer having a poly-uracil or poly-thymine sequence, which is able to bind molecules, such as RNA, having a polyadenylated terminal sequence.

The target-specific probe is preferably a polymeric group having a base sequence effective to specifically bind the target sequence. In one embodiment, the probe is polyanionic, for example, a polynucleotide or a polynucleotide analog. In a preferred embodiment, the probe has a nonionic backbone, for example, a morpholino oligomer or a peptide nucleic acid.

In another aspect, the invention provides a method for isolation or detection of a polynucleotide analyte molecule having a selected nucleotide target sequence in a polynucleotide-containing sample. According to the method, the sample is contacted with a rapid pairing reagent, which includes a solid substrate to which is linked a capture component effective to non-selectively bind polynucleotide molecules in the sample. Also linked to the substrate is a target-specific probe which is effective to selectively bind the target base sequence. The reagent is exposed to conditions effective to release polynucleotide molecules from the capture component under conditions which do not disrupt the linkage, formed via the target-specific probe, between the substrate and the target sequence.

The invention also provides a method of detecting the target sequence, in which, after release of non-analyte molecules, the rapid pairing reagent is exposed to a detectable reporter group which binds to the analyte molecule. Unbound reporter group is removed, and the reagent is examined for the presence of the reporter group. Preferably, the target-specific probe has a nonionic backbone, and the reporter group is a cationic reporter effective to electrostatically bind to the analyte molecule.

The method may also include isolation of the analyte molecule, in which, after release and removal of non-analyte molecules, the rapid pairing reagent is exposed to conditions effective to disrupt the substrate-probe-analyte complex. These conditions may include disrupting Watson-Crick base-pair hydrogen bonding between the probe and the analyte molecule. Alternatively, the probe may be linked to the substrate via a cleavable substrate-probe linkage which is not cleavable under conditions effective to cleave the linkage of the capture component. In this case, the rapid pairing reagent is treated with reagents effective to cleave the substrate-probe linkage.

For solid phase enzymatic amplification of a portion of the analyte molecule, the method further includes exposing the rapid pairing reagent to reagents effective for such amplification. These typically include polynucleotide primers, deoxynucleoside triphosphates, and a nucleic acid polymerase. In this case, the amplicon region of the analyte molecule, i.e., the region bound by primers, lies outside of the target sequence.

Although a preferred composition and method include a solid substrate having both capture component and target probe bound thereon, the invention also contemplates a method in which a sample having a target sequence is contacted with a first solid substrate having linked thereto a rapid capture component, effective to non-selectively bind polynucleotide molecules in the sample. The substrate with bound polynucleotide molecules is removed from the sample, and the molecules are released from the substrate and contacted with a second substrate having linked thereto a target-specific probe effective to bind selectively to the target sequence. To effect this release, the substrate is preferably exposed to conditions effective to release the molecules from the capture component without disrupting the substrate-probe-target linkage.

These and other objects and features of the invention will become more fully apparent when the following detailed description of the invention is read in conjunction with the accompanying drawings.

BRIEF DESCRIPTION OF THE DRAWINGS

FIG. 3 illustrates non-ionic probe types suitable for preparation of the target-specific probe, where

DETAILED DESCRIPTION OF THE INVENTION

I. Definitions

Figure 1:
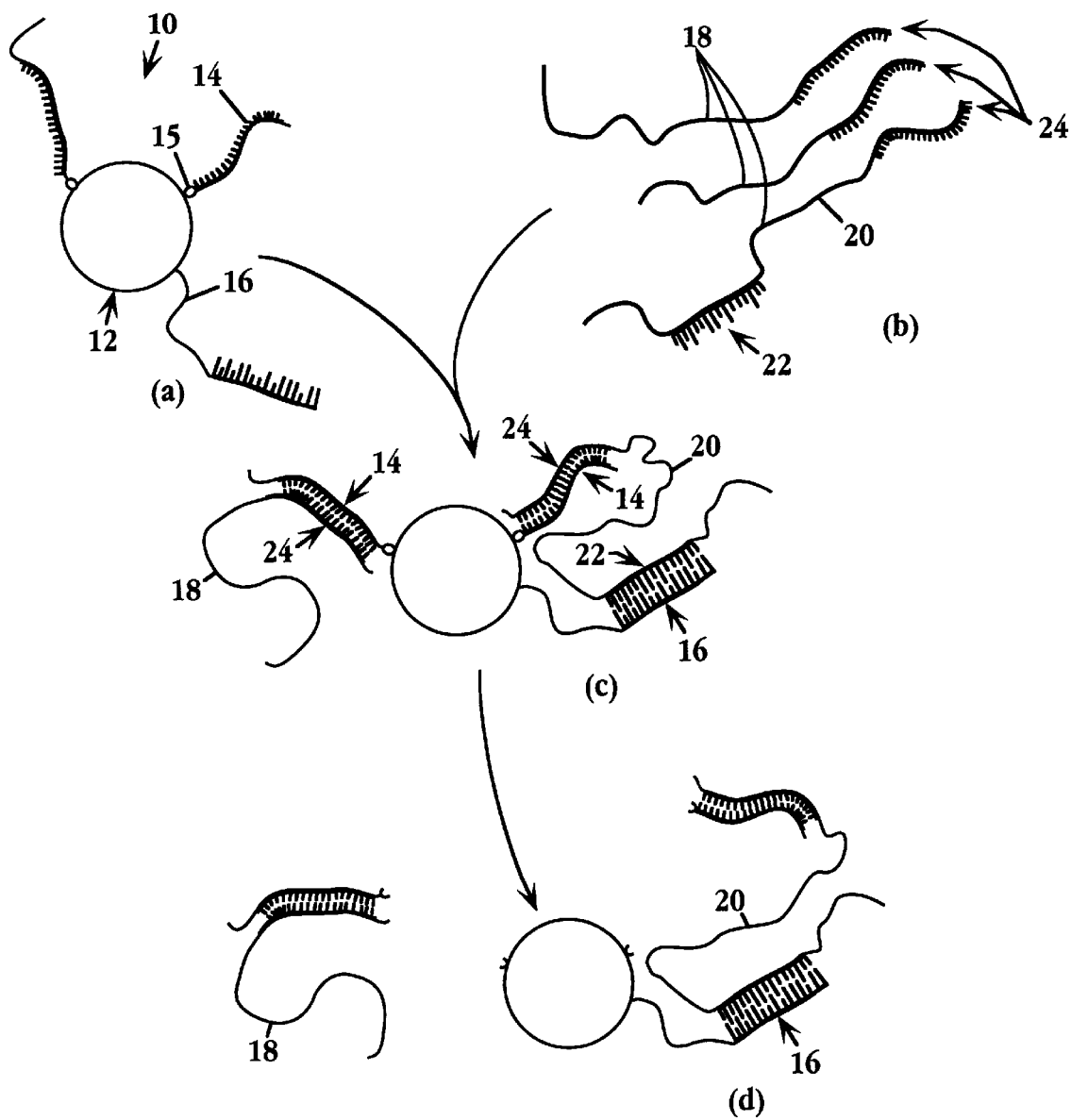
FIG. 1 illustrates a representative embodiment of the rapid pairing reagent and method of the invention.

The terms below have the following meanings unless indicated otherwise.

A "target-specific probe" is an oligomer effective for sequence-specific binding to a target sequence unique to an analyte polynucleotide. In most applications, the probe binds in a sequence-specific manner to a complementary sequence in the analyte molecule. In certain applications, it may be desired that the probe also bind to related but non-homologous sequences in the polynucleotide sample.

A "capture component" is a component which binds nucleic acids, or a subset of nucleic acids, in a rapid but non-specific manner. The subset of nucleic acids is typically a subset of non-homologous nucleic acids having a common sequence, such as poly-A tailed RNA molecules.

A "rapid-pairing reagent" is a reagent comprising a surface component, such as particles, fibers, a micro-titer well, a dipstick, a filter, a screen, or other solid or porous material, or combination thereof, to which is linked a capture component and a target-specific probe.

II. Rapid Pairing Reagent

The rapid-pairing reagent of the invention, as illustrated schematically at 10 in FIG. 1(a), includes a solid or porous surface 12 to which is linked a capture component 14, preferably via a cleavable linker 15, and a target-specific probe component 16. The nonspecific capture component is effective to rapidly and non-specifically bind polynucleotide molecules, and is designed such that polynucleotides can be released from this component under conditions which do not release analyte, or target sequences thereof, from the target-specific probe.

In using the rapid pairing reagent, specimen polynucleotides 18, shown at (b), are contacted with the reagent under conditions effective for capture of specimen polynucleotides, or a subset thereof, by the rapid-capture component 14. Analyte molecules 20 present in the specimen include the target sequence 22, represented in FIG. 1 by unevenly spaced lines, which is effective to bind specifically to a complementary sequence on probe component 16. Each of the polynucleotides, in one embodiment of the method, also contains a non-specific binding site, such as a poly-A tail, represented by evenly spaced lines in FIG. 1. In this embodiment, the capture component 14 comprises a poly-U sequence.

By virtue of this non-specific binding to the rapid pairing reagent, analyte molecules in the specimen are isolated from non-nucleotide sample components, and are positioned in close proximity to target-specific probe 16, linked to the same surface as rapid capture component 14. This results in a very high effective concentration of analyte in the vicinity of target-specific probe 16 and enables very efficient sequence-specific pairing between the probe and target sequence 22, as shown at (c) in FIG. 1.

As further illustrated in FIG. 1(d), non-target polynucleotides are selectively released from the capture component following probe-target pairing, preferably via cleavage of linkers 15, to leave only analyte 20, or target sequence 22 thereof, bound to the rapid-pairing reagent. Analyte so isolated can be utilized for a variety of purposes, including amplification or direct detection.

The rapid pairing reagent thus incorporates a surface component, a capture component and an analyte-specific probe component interspersed thereon, and a means for selectively releasing non-analyte polynucleotides. These various components and their use are described below.

A. Surface Component

The surface component of the capture reagent has functional sites suitable for attachment of both the capture component and the analyte-specific probe component. The surface should afford little or no non-specific binding of polynucleotides, and oligocationic reporters, if used. Alternatively, the surface may be structured such that any non-specific binding which does occur can be easily disrupted. Representative surfaces include microtiter wells, dip sticks, filters, screens, fibers, microparticles, and other solid and porous materials. Preferred surfaces are regular and present a large surface area per unit volume of specimen.

Small-diameter non-porous spheres are particularly preferred. Because of their regular surfaces, such spheres afford minimal undesired trapping of polynucleotides and cationic reporters, and because of their large surface-to-volume ratio, they can achieve rapid and thorough capture of specimen polynucleotides in the initial capture step. Diameters of 1–50$\mu$ are preferred, with diameters of 1–5$\mu$ particularly preferred. Although spheres as small as 0.1$\mu$ or less can be used, efficient recovery of such particles may be problematic.

Surfaces presenting carboxyl, hydroxyl, or amine moieties are particularly preferred because of the ease with which they can be derivatized. Glass beads, for example, are readily functionalized with aminosilane reagents. Before, during, or after attachment of the capture and target-specific probe components, it is often desirable to modify the surface so as to minimize undesired retention of the various components to which said surface will be exposed during use. One method for achieving a reduction in binding of undesired components is by covalently linking polyethylene glycol to said surface by methods known in the art (Harris, 1992).

In one embodiment, the surface component of the rapid-pairing reagent constitutes magnetic particles, and after reporter has been added to label the analyte strand, or target sequences thereof, unbound reporter may be separated from the rapid-pairing reagent by use of a magnetic field to sequester the rapid-pairing reagent while the unbound reporter is washed away, or by use of a magnetic field to pull the rapid-pairing reagent through a suitable wash solution. This procedure serves to reduce background signal due to unbound reporter to exceedingly low levels. Streptavidin-coated magnetic particles suitable for this purpose are available from Dynal (Oslo, Norway) under the trade name Dynabeads™. Ultra small magnetic particles, referred to as ferrofluids™, are available from Immunicon Corporation (Huntingdon Valley, Pa.).

B. Rapid-Capture Component

1. Electrostatic Binding. Nucleic acids, or a subset of nucleic acids, can be rapidly bound to a solid surface by a variety of methods. One method utilizes cationic moieties, preferably positively charged amines, linked to a surface for very rapid electrostatic binding to the polyanionic backbones of nucleic acids.

The amine component of the capture reagent should be effective for electrostatic binding of polynucleotides at a pH above that where cytosine moieties of polynucleotides are significantly ionized, that is, about pH 4.0. It should also release said polynucleotides at a pH below where guanine and uracil or thymine moieties of nucleic acids are significantly ionized, that is, about pH 10.

When the reagent is to be used for detection of the analyte, or target sequences thereof, a cationic polyamine may be used as a reporter group, as described below. In this case, the weakly basic amine component should release nucleic acids at a pH where strongly-basic amines still effectively bind nucleic acids, typically about pH 9 to 10.

Preferably, the amine component of the capture reagent has a pKa value between about 4.5 and 8.0. When the pKa of the amine is above about 7, the amine is preferably tertiary, since primary and secondary amines with pKa values above about 7 generally fail to release much of their bound nucleic acids below about pH 9.

Figure 4:
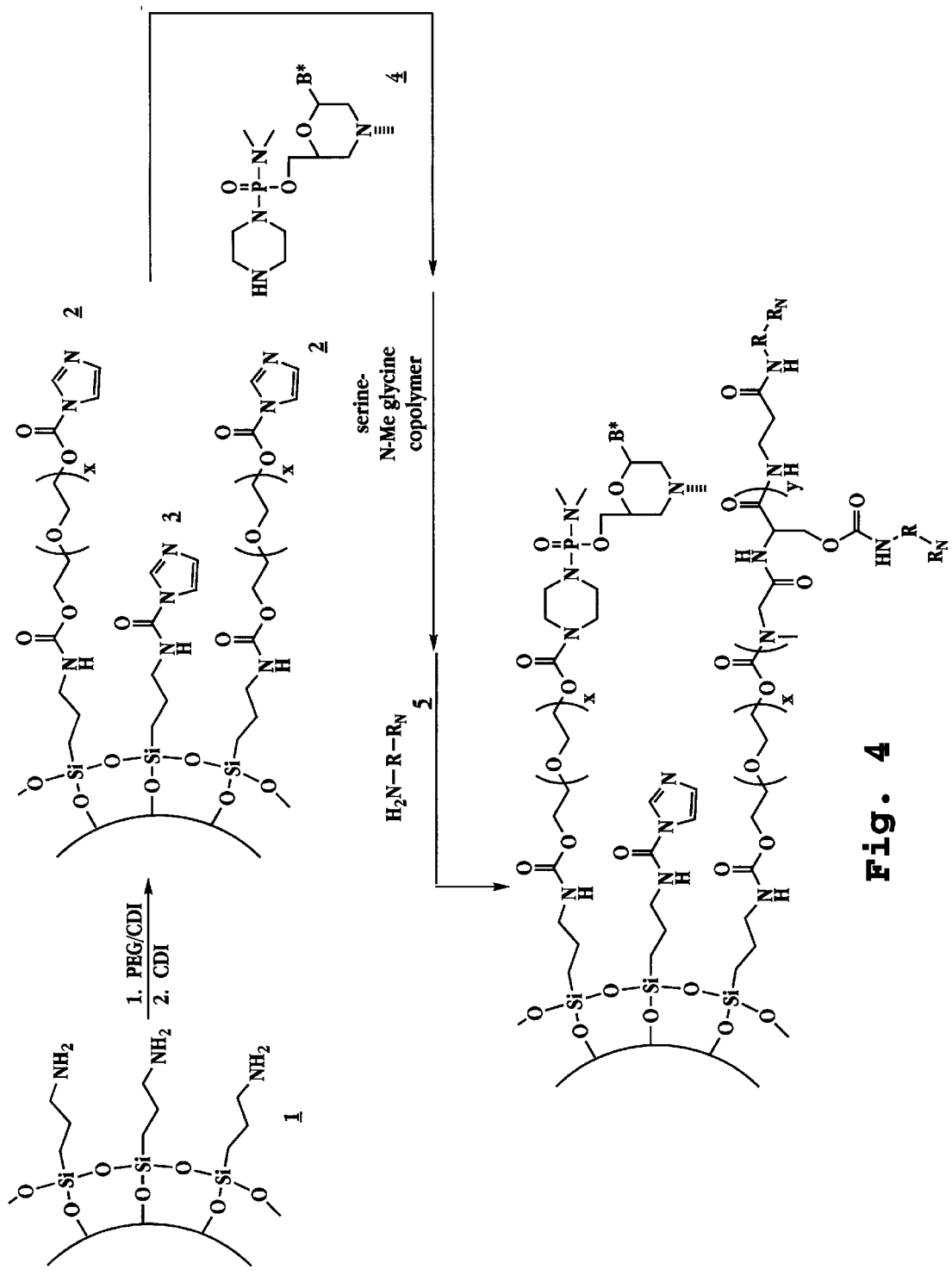
FIG. 4 illustrates the preparation of a capture reagent having weakly basic polyamine capture groups and nonionic morpholino target-specific probes.

The amine may be distributed in monomeric form over the surface of the capture reagent. However, the efficiency of binding is generally increased by incorporating the amines into oligomers, preferably comprising chains of about 5 to 30 amine moieties, sparsely distributed on the surface of the capture reagent. FIG. 4 illustrates a representative method, described in Example 2, for preparing an oligomeric amine component on a surface. The illustrated scheme employs a PEG spacer group, where x is preferably between about 8 and about 450, between the aminosilane surface groups and the oligoamines, which are linked through a carbonyl imidazoline moiety. The oligoamines, as shown, are conveniently prepared by functionalizing a serine-sarcosamine (N-methyl glycine) copolymer, where y is preferably between about 5 and about 50, with a weakly basic amine, represented by $H_2N\text{—}R\text{—}R_N$, or $H(CH_3)N\text{—}R\text{—}R_N$.

Figure 2:
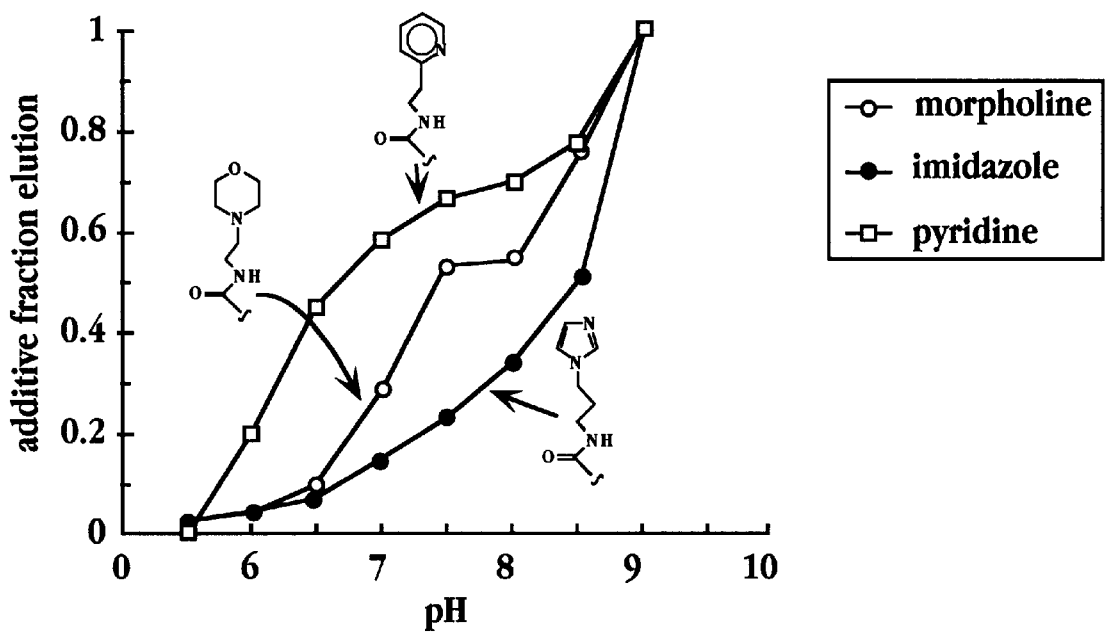
FIG. 2 illustrates the pH-dependent release of nucleic acids from weakly-basic amine components.

Preferred amines include those of the above formula in which R is an alkyl or alkyl ether residue, and $R_N$ is substituted or unsubstituted 2-, 3-, or 4-pyridyl, imidazolyl, piperazyl, or morpholino. $R_N$ may also be a weakly basic acyclic secondary or tertiary amine. Suitable amines for use in the capture component may be selected by binding an amine, in monomeric or oligomeric form, to a surface and evaluating the functionalized surface for binding and release of polynucleotides as a function of pH. Cellulose particles provide a convenient surface for this purpose. Example 1 describes a representative method for electrostatic capture of polynucleotides to surface-bound amines at low pH, and subsequent release as a function of pH. FIG. 2 illustrates the release of single-stranded DNA from several amine-derivatized cellulose surfaces as a function of the pH of the wash solution.

The amine component should be constructed such that it will not be degraded by substances, particularly proteases, endogenous in the specimen or added during specimen preparation. In particular, any oligomeric amine component should have a backbone structure which is not degraded by proteases, if said proteases are present in the specimen.

The amine components described thus far are weakly basic amines which bind or release oligonucleotides as a function of pH. Strongly basic amines may also be used as capture components, in conjunction with a chemically cleavable linkage, as described further below. In this case, release is effected by selectively cleaving this linkage rather than by adjusting pH.

In another variation, suitable for use in high ionic strength solutions, the cationic moieties can be attached to aromatic moieties which additionally stabilize the complex by intercalating between adjacent bases of nucleic acids. Methidium-sepharose beads, available from Gibco/BRL, are used for the capture of double-stranded nucleic acids. Single-stranded nucleic acids could be captured by a similar reagent based on, e.g., aurintricarboxylic acid, which is known to bind such molecules.

2. Binding via Watson/Crick Base Pairing. Another method for rapid binding of a subset of nucleic acids to the reagent surface employs uracil- or thymine-containing homopolymers, which bind the polyadenylic acid tails of eukaryotic mRNA molecules via Watson/Crick pairing. Although effective only for mRNA, this method is more selective than electrostatic binding, which may bind other negatively charged species within a polynucleotide-containing sample. A selectively cleavable linker, as described below, is preferably provided between the probe and the reagent surface.

The uracil or thymine homopolymer may be an oligonucleotide, for example, oligo(dT), or a nonionic oligomer. A morpholino oligomer containing uracil bases, which is an example of the latter, is designated herein as oligo(mU). As will be described below in the discussion of target/probe pairing (Section C), a non-ionic morpholino oligomer is advantageous in that the rate of binding to a probe sequence is relatively independent of salt concentration. Preparation of such oligomers is described in U.S. Pat. No. 5,185,444 (Summerton and Weller, 1993), which is hereby incorporated by reference.

C. Analyte-Specific Probe Components

The probe component of the rapid capture reagent is a polymeric moiety having a base sequence effective for sequence-specific binding to the target sequence. For single-stranded analytes, this binding is via Watson/Crick hydrogen bonding between the bases of the probe and the bases of the target sequence of the analyte strand. For double-stranded nucleic acids, this binding is via hydrogen bonding between the polar-major-groove sites of the base-pairs of the target sequence and the base-pair-recognition moieties of the probe (Summerton and Weller, 1995).

Target specific probes comprising sequences of DNA, RNA, 2'-O-alkyl RNA, etc., may be used in conjunction with oligo-U or oligo-T capture components, described above. However, in order to preclude binding of the probe to an amino-containing capture reagent, or to a cationic reporter group, it is preferred that the backbone of said probe be largely non-ionic under the conditions of use.

Representative non-ionic probe structural types which can be used for binding single-stranded target sequences include a variety of nucleic acid analogs, such as phosphotriester- and methylphosphonate-linked DNA (Miller et al., 1971, 1981), carbamate-linked DNA (Stirchak et al., 1987, 1989), and phosphoroamidate-linked DNA (Froehler, 1988). These non-ionic nucleic acid analogs, however, bind their target sequences with appreciably lower affinities than do corresponding natural nucleic acids. As a consequence, in diagnostic applications where the probe-bound analyte is to be detected, hydrodynamic shear forces created during wash steps preclude all but modest-sized reporter groups, thereby greatly limiting the amount of signal which can be generated per analyte copy. The sensitivity of systems utilizing such non-ionic nucleic acid analog probes is consequently limited.

Figure 3A:
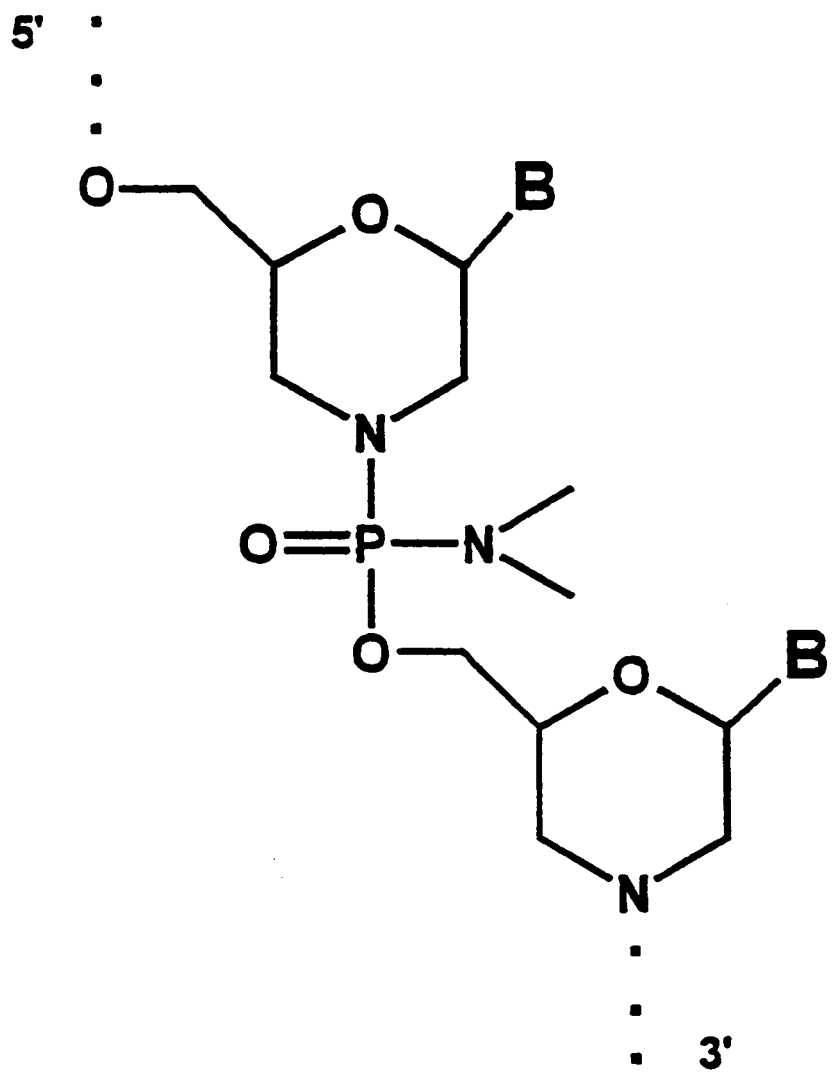
FIG. 3A shows a preferred non-ionic morpholino probe for binding single-stranded analytes.

In order to obtain a larger reporter signal per analyte copy in diagnostic applications, the preferred probe component of the capture reagent should have a high affinity for its target sequence. In this regard, two non-ionic probe structural types which afford exceptional target binding affinity, especially for RNA targets, are available. These two preferred probe structural types are referred to as morpholino oligomers, or simply morpholinos, such as illustrated in FIG. 3A (Summerton and Weller, 1993), and peptide nucleic acids, or PNAs (Nielsen et al., 1991). These probe types are not analogs of nucleic acids because they lack the 5-membered ribose or deoxyribose sugar characteristic of nucleic acids and analogs thereof.

As shown in Summerton and Weller, 1993, several types of nonionic linkages may be used to construct a morpholino backbone. A phorphoramidate linkage, such as shown in FIG. 3A, is preferred.

The morpholino and PNA probes are preferred for diagnostic applications of the invention because, as a consequence of their high target binding affinities, they can retain relatively large reporters during wash steps, and thereby provide a large reporter signal per copy of analyte polynucleotide in the specimen. This results in substantially greater sensitivity than can be achieved with corresponding non-ionic DNA and RNA analogs.

Figure 3B:
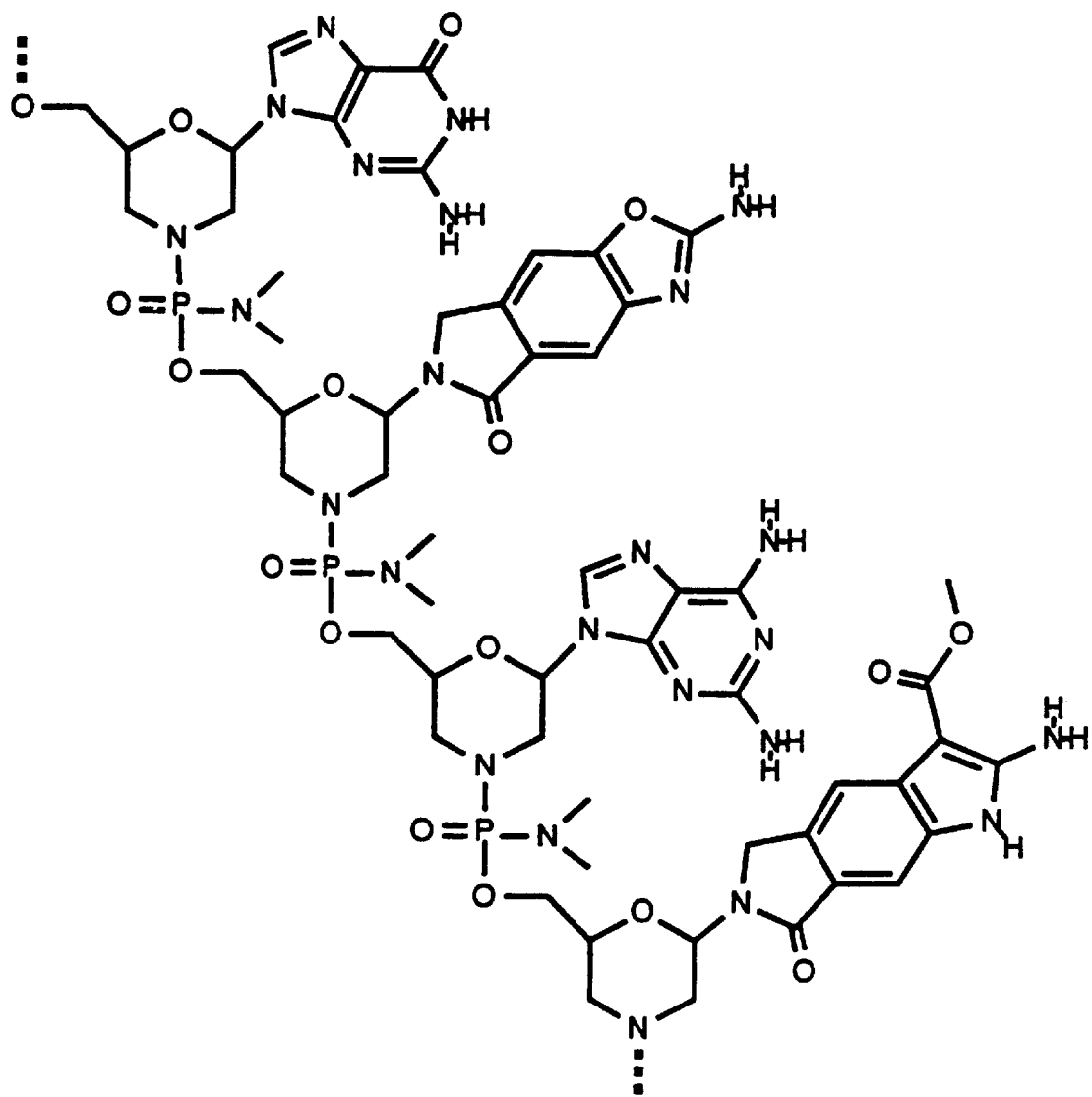
FIG. 3B shows a preferred non-ionic probe for binding duplex-DNA analytes.

When the analyte is double-stranded DNA, the need for a strand-separating step can be avoided by using a non-ionic probe designed for sequence-specific binding to major-groove sites in duplex DNA. FIG. 3B illustrates one such probe type, whose preparation is described in U.S. Pat. No. 5,166,315 (Summerton and Weller, 1992), which is hereby incorporated by reference.

In principle, the non-ionic probe can be linked directly to the surface component of the capture reagent. However, linking the probe to a long hydrophilic spacer group, which is in turn linked to the surface component, allows the probe better access to target sequences, particularly in analyte molecules electrostatically bound to a weakly-basic amine component of the capture reagent, and in very large analyte molecules. Polyethylene glycols with molecular weight averages ranging from about 400 to 20,000 daltons are particularly suitable as spacer groups for this purpose.

FIG. 4 illustrates a representative method, described in Example 2, for preparing a capture reagent comprising a solid silica particle to whose surface is linked a weakly-basic oligomeric amine capture component, and a non-ionic morpholino probe component, which are tethered to said silica particle via a long polyethylene glycol chain. In this procedure, a silica particle is functionalized with an aminosilane, according to well known procedures, to give activated particle 1. Reaction with polyethylene glycol and carbonyldiimidazole (CDI), followed by excess CDI to cap remaining sites, gives activated PEG chains 2 and capped sites 3 on the particle surface. The piperazine-terminated morpholino oligomer 4, of which only one subunit is shown, is added to activated chains 2. At the same time, or subsequently, oligoamine capture components are added, as shown, giving the final functionalized capture reagent.

Examples 3 and 4 describe the preparation of a capture reagent having nonionic morpholino oligomers as both capture and target-specific probe components. In these preparations, a 1:1 ratio of target-specific probe to capture probe was used. Studies in support of the invention have shown that ratios of 1:1 to 4:1 are preferred, and a ratio between about 2:1 and 3:1 is particularly preferred, for optimization of both total polynucleotide capture and specific analyte capture.

D. Release Mechanisms

To accomplish selective retention on the reagent surface of a target sequence-containing polynucleotide, the nonselective binding of the capture reagent to the polynucleotides must be selectively cleavable, that is, it is cleavable under conditions which do not release the target molecules, bound in a sequence-specific manner to the probe, from the reagent.

When the capture component is a weakly basic amine, selective cleavage is achieved by raising the pH of the solution to a value above the pKa of the binding amine (but not high enough to disrupt base-pair hydrogen bonding), as described in Section B1, above. Binding of intercalating amines may be disrupted by decreasing solvent polarity and increasing ionic strength. With most other capture groups, including, for example, strongly basic amines, oligo(dT)'s, and oligo(mU)'s, a cleavable linkage, as shown at 15 in FIG. 1, is preferably provided between the capture component and the reagent surface.

A cleavable linkage may also be provided between the target-specific probe and the reagent surface, if it is desired to release the analyte molecule from the reagent surface. The analyte may also be released by exposing the reagent to conditions which will disrupt Watson/Crick base-pair binding between the analyte and the probe. Such conditions include heat, high pH (e.g. 12 or higher), or treatment with a denaturant such as formamide. However, greater selectivity is provided by using a selectively cleavable chemical linker, as described below. In any case, conditions used to release polynucleotides from the capture component must not be effective to disrupt the surface-probe-analyte complex, that is, to release the analyte target sequence from the solid substrate.

A number of chemical linking groups, cleavable by specific reagents or conditions, are well known in the art. These include, but are not limited to: a disulfide linkage, cleaved by a sulfhydryl (eg., dithiothreitol, or DTT); an orthonitrobenzyl ester, photochemically cleaved by 320 nm light; vicinyl hydroxyls, cleaved by periodate; esters, cleaved by esterases; peptides, cleaved by peptidases or proteases; and oligosaccharides, cleaved by glycosidases. A cleavable linker must of course not be cleaved by species, such as enzymes, which may be present in the sample.

In a preferred embodiment, the capture component is linked to the reagent surface, or to a spacer group attached to the surface, via a disulfide linkage. Optionally, a second cleavable linkage connects the target-specific probe to the reagent surface.

III. Rapid-Pairing Method

The preferred embodiment of the method incorporates the basic steps of (i) contacting the polynucleotide-containing sample with the rapid pairing reagent, such that binding occurs to both the rapid capture component and the target-specific probe, and (ii) releasing non-specifically bound molecules from the rapid capture component. Additional steps may include detecting the target sequence by adding a detectable reporter group, isolating the analyte molecule by releasing it from the target-specific probe, subjecting the analyte molecule to enzymatic amplification, or a combination of these procedures. Preferred methods of carrying out these steps are described in detail below.

Although a preferred method employs a rapid pairing reagent having both a rapid capture component and a target probe, the invention also contemplates a method in which the sample is first contacted with a first solid substrate containing a rapid capture component. The rapid capture component binds polynucleotide molecules, and the substrate is then removed from the sample, e.g. by filtration, thereby isolating polynucleotides from non-polynucleotide sample components and increasing their concentration. The molecules are then released from the substrate and contacted, in their highly concentrated state, with a second substrate containing a target-specific probe. To effect this release, the first substrate is preferably exposed to conditions which release the molecules from the capture component without disrupting the linkage between the second substrate, probe, and analyte molecule. In this way, non-analyte molecules may be released in the presence of the second substrate.

Finally, the second substrate, with bound analyte molecules, is removed from the system. Preferably, the second substrate is of a material easily separated from the first substrate, such as a magnetic material.

Although this method presents some of the advantages of the preferred method, i.e., isolating polynucleotide molecules from the sample and increasing their concentration, the proximity achieved between the analyte molecule and the target-specific probe is expected to be several orders of magnitude less than in the preferred method, where both the rapid capture and target-specific components are included in close proximity on the same substrate. In this case, the analyte molecule is preferably able to concomitantly bind to the rapid capture component and the target-specific component, as shown in FIG. 1.

A. Sample Preparation

Generally, before utilizing the method of the invention, a specimen must be treated in order to release nucleic acids from biological structures. This can be accomplished by a variety of methods known in the art. Preferably, the cellular, subcellular, or viral structure of interest is disrupted in the presence of the rapid pairing reagent, as long as such treatment does not expose the reagent to species which would degrade chemical linkages therein.

When the analyte is DNA and the specimen contains said DNA in a double-stranded state, and the probe of the capture reagent is designed for Watson/Crick pairing to single-stranded nucleic acids, the duplex DNA must be strand separated before utilizing the method of the invention. Such strand separation can be effected by heating the sample to well above the melting temperature of the DNA duplex. Alternatively, addition of alkali to give a pH of 12 or above rapidly disrupts DNA duplexes. It is often also desirable to dispose of proteins, particularly nucleases, in the specimen. Pronase or protease K, often combined with detergent, are generally effective for this purpose.

B. Rapid Capture

When the capture reagent comprises a weakly basic amine, the solution containing specimen polynucleotides is adjusted to a pH at which the capture reagent is effective to electrostatically bind polynucleotides. While the optimal pH for this purpose is dependent on the particular weakly-basic amine component used in preparing the capture reagent, as well as whether said amine is in a monomeric or oligomeric form, the pH for effective electrostatic capture is typically in the range of 4 to 7. This pH adjustment can be readily carried out as part of the specimen preparation step, simply by incorporating in the specimen receiving container a suitable buffer, preferably in dry form, effective to adjust the specimen to the proper pH for electrostatic capture of polynucleotides.

The salt content of the solution may also be adjusted to promote optimum binding of polynucleotides to the capture reagent. In the case of a weakly basic amine capture reagent, a low salt environment increases electrostatic attraction between the oppositely charged capture reagent and polynucleotide molecules. Binding of strongly basic and intercalating amines is less sensitive to ionic strength.

When a polynucleotide capture reagent (e.g., oligo(dT) or oligo(dU)) is used, binding may be slow under low salt conditions, due to electrostatic repulsion between the polyanionic capture reagent and polynucleotides. When a non-ionic oligomer, e.g. an oligo(mU) is used, salt sensitivity is greatly decreased, as discussed further below in Section B.

The capture reagent can be present during the initial specimen preparation process, especially when the surface component comprises particles, so that capture occurs as soon as the specimen polynucleotides are released from biological structures and the pH reaches the appropriate value. Alternatively, the specimen may be poured through a filter or screen, or over a bed of microparticles, constituting the capture reagent. Still further, the contacting can be accomplished by inserting into the specimen a dipstick constituting the capture reagent, or by adding the specimen to a microtiter well or other container whose surface constitutes the capture reagent.

C. Probe-Target Pairing

The specimen is preferably contacted with the capture reagent under conditions which enable binding to the capture component as well as the target-specific component. As noted above, sensitivity of binding to ionic strength depends on the type of probe used.

Under high salt conditions, or in the presence of divalent cations, nucleic acids, and particularly RNA, contain appreciable secondary structure which can limit the extent of probe-target pairing and significantly slow the rate at which such pairing occurs. Because secondary structures in nucleic acids position backbone phosphates in relatively close proximity, these structures can be easily disrupted by reducing the salt concentration and/or by sequestering divalent cations, with EDTA or citrate, for example. These steps serve to unmask the anionic phosphates, and the resulting electrostatic repulsion between proximal phosphates disrupts the hydrogen bonding largely responsible for secondary structure. However, such low salt conditions also increase the effect of electrostatic repulsion between a target nucleotide sequence and a polynucleotide probe, as illustrated in FIG. 5.

Figure 5:
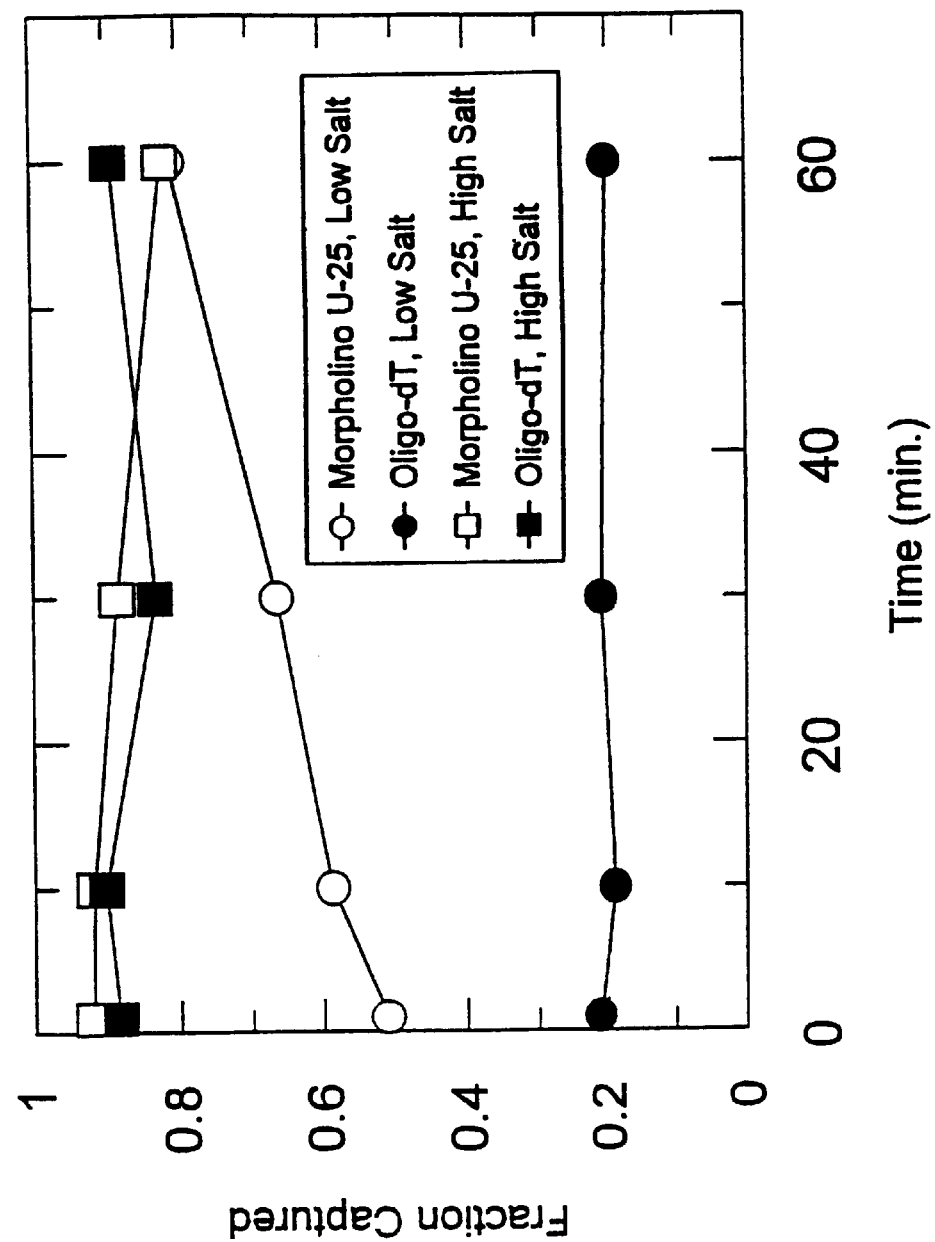
FIG. 5 shows the extent of capture of a poly-A RNA sequence by a polynucleotide probe and by a non-ionic morpholino probe at high and low ionic strength.

In contrast to the pairing of a polyanionic probe, e.g. oligo(dT), to a target sequences to form a nucleic acid duplex, pairing of a non-ionic probe to a complementary nucleic acid target sequence is only moderately reduced under low salt conditions, as illustrated in FIG. 5 and described in Example 5. Even under near-neutral conditions, there is little or no electrostatic repulsion between the non-ionic probe and its poly-anionic target sequence. Other studies in support of the invention have shown that the morpholino probes hybridize to DNA targets with kinetics which are not dependent on salt concentration. Therefore, it is likely that the somewhat slower binding at low ionic strength, shown in FIG. 5, is due to an effect of the substrate, rather than the probes.

A preferred embodiment of the method thus includes a wash with a solution having a low pH, to retain analyte binding by a weakly-basic amine component, and low ionic strength, to disrupt secondary structure in the analyte. The target probe is preferably nonionic and thus effective to bind DNA or RNA efficiently at low ionic strength. The solution may also contain reagent effective for sequestering divalent cations, to further assist in disrupting analyte secondary structure. Such a wash step often appreciably increases both the rate and the extent of probe-target pairing.

Probe-target pairing may generally be carried out at room temperature. In conventional capture strategies, capture at or above the $T_m$ of the probe/target complex is preferable for high selectivity (high signal-to-noise), although capture is more efficient below the $T_m$. The rapid-pairing reagent of the invention prevents the advantage of allowing efficient and selective capture below the $T_m$ of the probe/target complex. However, if increased selectivity is required, e.g. to resolve single-base changes, higher temperatures may be used.

D. Release From the Rapid-Capture Component

When a weakly-basic amine rapid-capture component is used, non-specifically bound molecules are released by raising pH to a value at which the weakly-basic amine no longer binds polynucleotides. This value is typically substantially above the pKa of the amine but below a pH which will disrupt base-pair binding (e.g. pH 12). As noted above, binding of intercalating amines may be disrupted by decreasing solvent polarity and increasing ionic strength.

For greatest selectivity in release, a selectively cleavable linkage is provided which may be cleaved under conditions which do not disrupt probe/target pairing. As noted above, a disulfide linkage, cleavable by DTT, is useful for this purpose. Utilization of such a linkage is described in Examples 3 and 4.

E. Release of Analyte Molecules

Where the analyte molecule is to be isolated, a selectively cleavable linkage is preferably provided between the target-specific probe and the reagent surface. Again, a disulfide is a useful linking group, unless such has been used to link the capture group to the reagent surface, whereupon a separately cleavable linker, such as a diol or photochemically cleavable group, should be used. This technique has the advantage of high selectivity, although the probe component remains bound to the isolated analyte molecule.

The target molecule may also be released by treatments which dissociate Watson-Crick base pairing. These include heating to a temperature greater than the $T_m$ of the duplex (e.g. up to 95° C.), treating with a denaturant, such as formamide, DMSO, urea, or a guanidinium salt, or treatment with strong base, such as 0.1 N $NH_4OH$. Strong base should not be used with RNA analytes, which are unstable at high pH.

Such methods are preferable if the analyte is to be isolated without the probe moiety remaining bound to the target sequence. However, selective cleavage of a probe-analyte linkage generally reduces the risk of contamination from residual non-analyte molecules on the reagent surface, and thus may result in a cleaner analyte isolate than release by the above-mentioned denaturation methods.

IV. Applications

A. Selective Capture of Target RNA

1. Capture of α-Globin RNA. As an illustration of the method, capture particles were prepared by binding morpholino oligomers to the surface of magnetic beads (M-280), as described in Example 3. A first particle contained a $U_{25}$ probe (a 25-mer poly-uracil morpholino oligomer, SEQ ID NO: 1) bound via a PEG spacer group and a disulfide linker group. A second particle contained a probe, designated Neu-Probe™ 124, complementary to an α-globin RNA transcript (SEQ ID NO: 2). A third particle, constituting the rapid pairing reagent, contained both probes. Also included were M-280 beads having no attached probes, as a control for nonspecific sticking to the particles.

Two RNA transcripts, the α-globin transcript and an HIV-CP1 transcript used to determine non-specific capture, were prepared as described in Example 3. The transcripts were diluted in capture buffer, and each preparation was treated with each of the four particles described above.

As described in Example 3, only the particles containing $U_{25}$ probe captured significant amounts of RNA transcripts, both α-globin and HIV-1 sequences. In the succeeding release step, designed to release non-target RNA, the α-globin sequences were largely released from beads which contain only $U_{25}$. Much less RNA was released from beads containing the α-globin specific sequence (Neu-Probe™ 124, SEQ ID NO: 2) in addition to the $U_{25}$. HIV-1 RNA was released from beads containing $U_{25}$ only and from those containing the combination of Neu-Probe™ 124 and $U_{25}$.

These results showed sequence-specific capture of α-globin poly-A RNA by an α-globin specific capture probe, but not of a poly-A HIV-1 RNA, which was non-homologous to the specific capture sequence. The combination of sequence-specific probe and rapid capture component ($U_{25}$) resulted in significantly more efficient capture than the sequence-specific probe alone, and in sequence-specific purification of α-globin sequences from the mixture of α-globin and HIV-1 RNA transcripts.

2. Capture of HIV-1 RNA in Plasma Lysate.

As a further illustration of the method, capture particles were prepared by binding morpholino oligomers to the surface of magnetic beads, as described in Example 3. A first particle contained the $U_{25}$ probe (SEQ ID NO: 1) described above, bound via a PEG spacer group and a disulfide linker group. A second particle contained an HIV-CP1 specific probe, having the sequence UUU AAA UCU UGU GGG GUG GCU CC (SEQ ID NO: 3), and a third contained both probes. The beads were added separately to plasma lysate samples containing radiolabelled target RNA (poly-A tailed HIV gag RNA) and non-target RNA (rabbit α-globin RNA).

Figure 6:
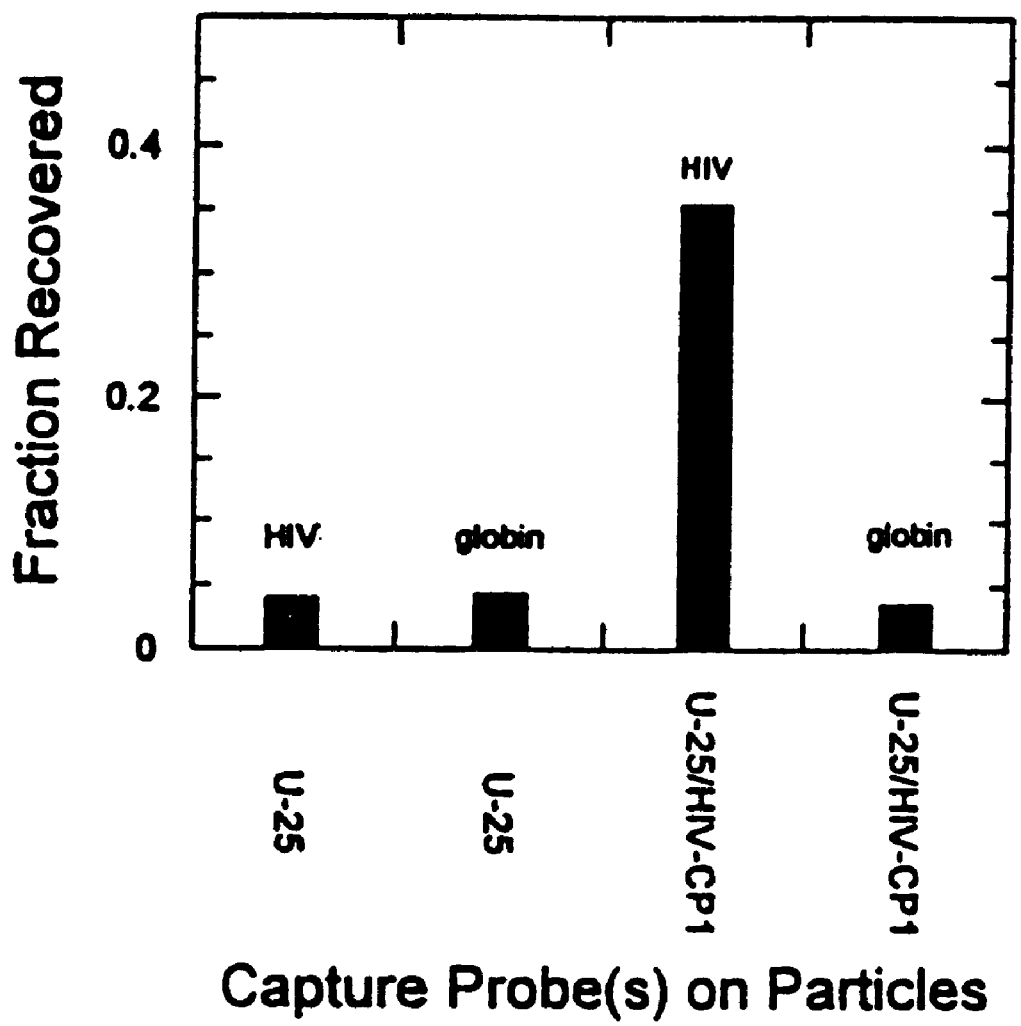
FIG. 6 illustrates selective capture of an HIV RNA transcript by a rapid pairing reagent having a poly-U capture reagent and an HIV-specific probe, in accordance with one embodiment of the invention.

After incubation, beads were magnetically separated and treated with DTT to cleave the disulfide linkage. As shown in FIG. 6, particles containing only a $U_{25}$ probe retained small and equivalent amounts of both RNA types, while the particles containing both probes retained target RNA to a much greater degree. Very slow hybridization was observed to particles having only target-specific probe (data not shown). These results demonstrate accelerated overall binding by the capture probe and selective retention of RNA bound through the target-specific probe. The method as described is applicable to any mRNA containing a poly-A tail or any viral genome containing a poly-A sequence.

Increased recovery of target RNA (51% vs. 37%) was achieved by using capture reagents containing multiple HIV-specific target probes (designated CP1, CP2, and CP3; SEQ ID NOS: 3, 4, and 5, respectively), as described in Example 4. Reagents containing multiple probes are particularly preferred for capturing very long nucleic acids, such as genomic DNA. The use of spacer groups such as PEG is also likely to facilitate capture of such molecules by avoiding the necessity of very close approach to the surface of the solid substrate.

B. Enzymatic Amplification of Analyte

The present method is particularly useful for isolation of sequences for enzymatic amplification. Sample preparation continues to represent the bulk of time and labor expenditure in such applications. In particular, the isolation technique must not co-extract substances which inhibit DNA polymerases. These include heparin and heme, which are frequently encountered in clinical specimens, as well as glycoproteins and high levels of albumin. Non-homologous DNA can also reduce the efficiency of PCR.

Figure 7:
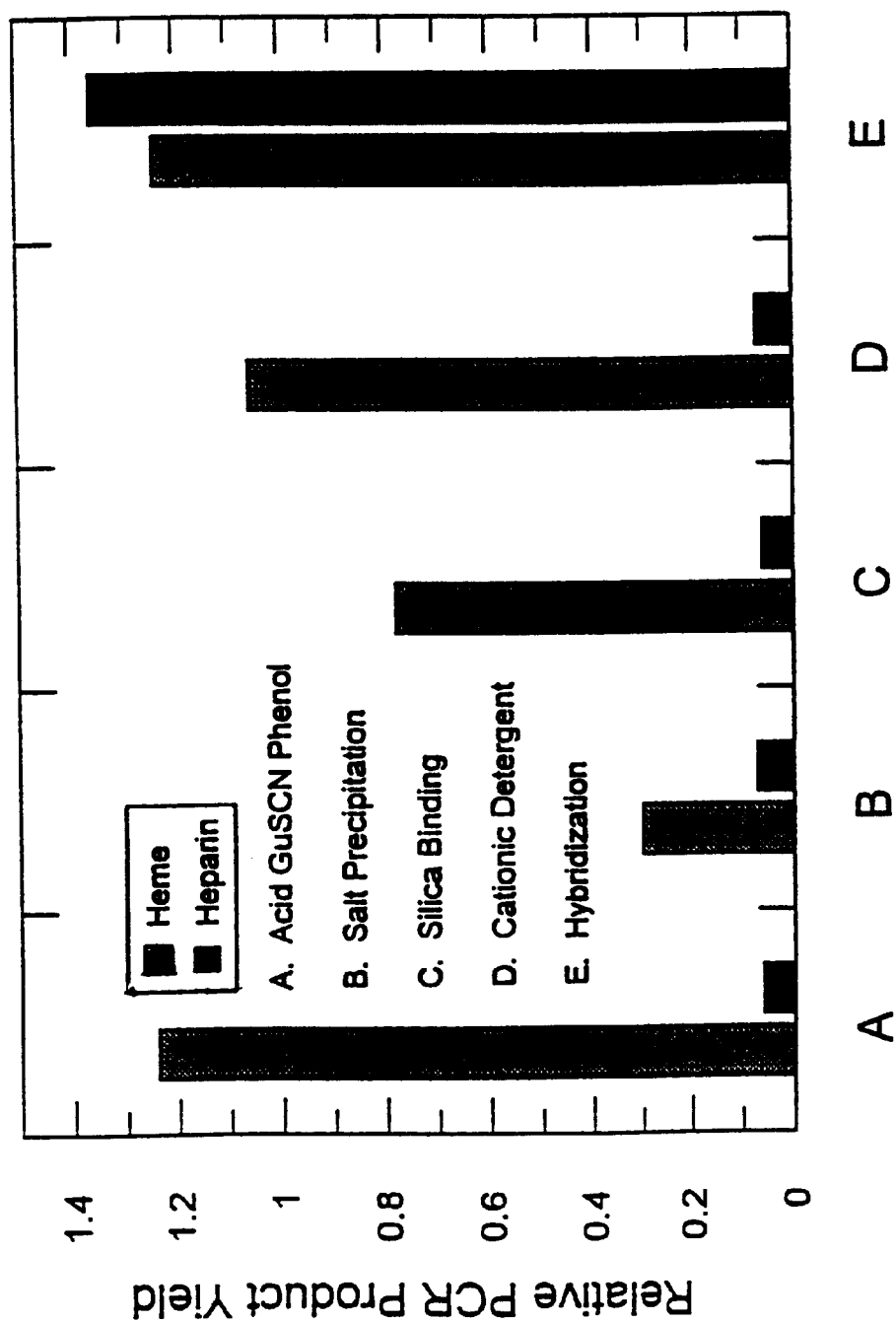
FIG. 7 shows PCR product yields of RNA from plasma spiked with heme and heparin and purified via various isolation methods including hybridization.

Current methods used for sample preparation, such as organic extraction, silica binding, and salt precipitation, make use of differential binding or solubility properties of nucleic acids and other sample components. Sequence-specific hybridization achieves a higher purification factor, as shown in FIG. 7. In this study (Example 6), samples spiked with heme and with heparin were purified by various techniques and amplified. Only purification by hybridization resulted in successful amplification in both cases. All of the other techniques co-extracted a substantial amount of heparin, resulting in almost complete inhibition, and some level of heparin.

A disadvantage of conventional hybridization is that, using only a sequence-specific probe coupled to a solid phase, it is generally very slow and inefficient, especially for low-copy sequences. The present invention, by combining rapid capture and concentration of polynucleotides with selective targeting of analyte molecules, greatly enhances this process. An additional advantage of a preferred embodiment of the invention, wherein nonionic morpholino oligomers are used for target-specific probes and/or capture component, is that such oligomers are not extended by polymerases and will not interfere with amplification of the target molecule.

Sequences isolated by the present method are suitable for amplification by such techniques as PCR, strand displacement amplification (SDA), nucleic acid sequence based amplification (NASBA), or other techniques known in the art. Amplification may conveniently be carried out without release of the analyte molecule from the rapid pairing reagent, as long as the amplicon region (i.e., the region bound by primers) is outside of the target sequence bound to the target-specific probe, as described in Example 4.

Such a solid-phase process is generally more easily automated, as long as the particles may be easily kept in suspension. Particularly useful for this purpose are particles of small size and suitable surface charge to avoid settling or clumping, including especially ferrofluids™, as provided by Immunicon Corp., Huntingdon Valley, Pa.

In carrying out the method, following removal of non-target molecules from the capture component of the reagent, the solid phase containing the analyte molecule is contacted with components necessary for amplification, according to techniques known in the art. These components typically include suitable primers, deoxynucleoside triphosphate sub-units (dNTP's), a compatible buffer containing divalent metal ions, and a polymerase, which may be DNA polymerase, a DNA-dependent RNA polymerase or reverse transcriptase, or an RNA-dependent RNA polymerase.

The analyte molecule may also be released from the reagent, if desired, by methods described above. It should be noted that cleavage of a linker group, as opposed to denaturatization methods, releases the analyte molecule with the probe still bound. The probe may subsequently be removed by heat treatment, however. If a morpholino probe is used, it will not interfere with the amplification process, as noted above.

C. Detection Of Analyte

In addition to serving as a sample preparation component of a diagnostic method, with or without amplification, the rapid-pairing method also provides a means for direct direction of the analyte on the solid reagent, due to the high degree of separation of an analyte containing a target sequence from non-target molecules. Although detection may be facilitated by amplification of the target sequence, as described in the previous section, high sensitivity detection methods may enable direct detection, thus greatly simplifying the detection process. Such methods include those using chemiluminescence, which are able to detect as little as 0.1 amol (typically representing about $6 \times 10^4$ molecules) of analyte.

A preferred method of detection of nucleic acids captured by means of a non-ionic probe is described in U.S. Pat. No. 5,217,866 (Summerton and Weller). This method employs a labelled polycationic reporter which is capable of binding to the polyanionic backbone of nucleic acids without disrupting Watson-Crick base pairing. One type of polycationic reporter is polyethyleneimine conjugated to a detectable group, e.g. an enzyme, a fluorescent group, or a chemiluminescent or other luminescent molecule. Alkaline phosphatase is a preferred enzyme for this purpose, using a chemiluminescent dioxetane substrate, such as CDP-Star™ (Perkin Elmer, Tropix Division, Bedford, Mass.) for detection. Horseradish peroxidase may also be used, using a chemiluminescent peroxidase substrate, e.g. PS-1, PS-2, or PS-3 (Lumigen, Detroit, Mich.).

Figure 8:
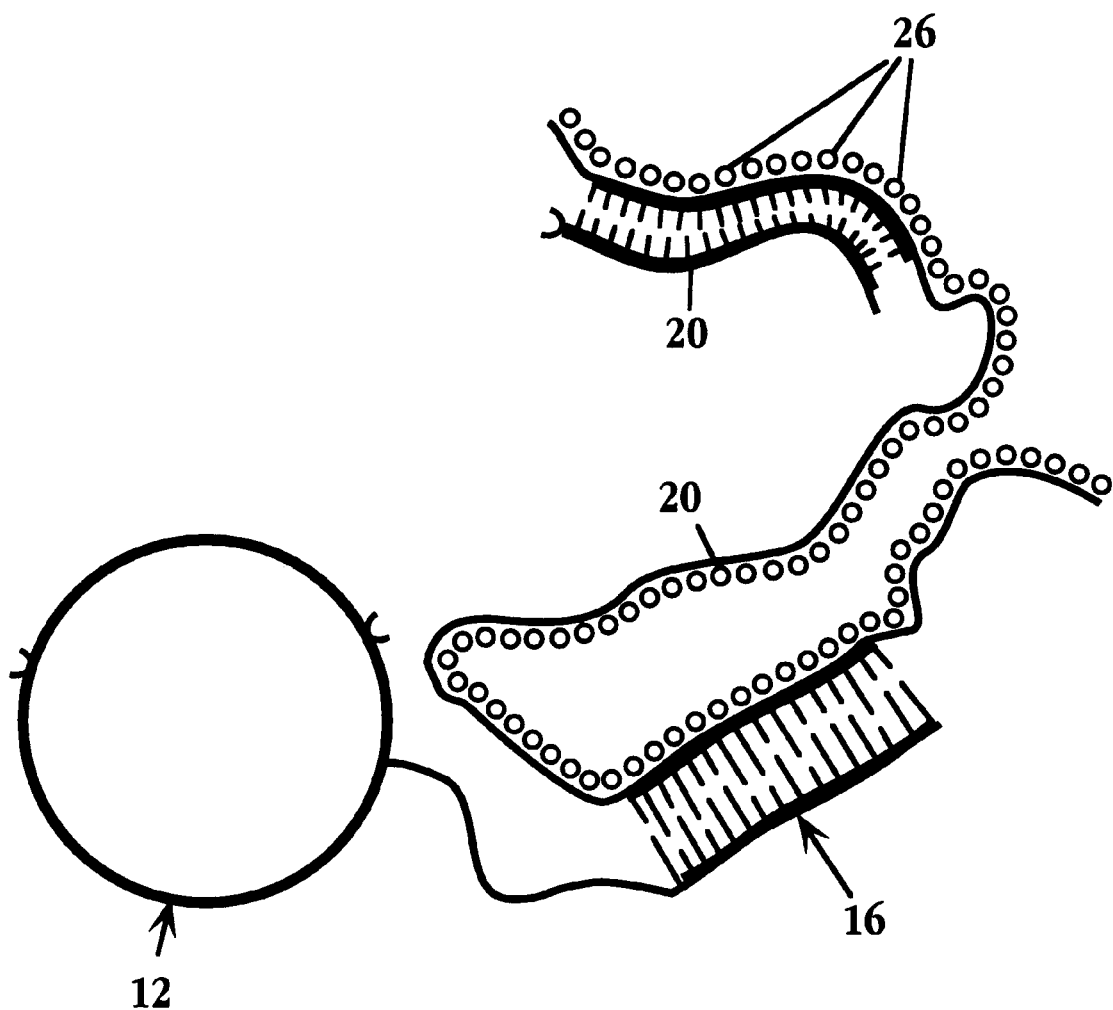
FIG. 8 illustrates detection of the probe-bound analyte with a cationic reporter.

In practicing the method, non-targeted molecules are released from the rapid capture reagent as described above, e.g. by raising solution pH above the pKa of a weakly basic amine capture group, or selectively cleaving a linker group between the capture group and the reagent surface. The substrate with bound analyte, shown schematically in FIG. 8, is then is isolated via simple filtration and/or washing steps. Cationic reporter 26 is added and rapidly binds to the polyanionic backbone of analyte molecules 20 bound to target-specific probes 16. Because the probes are nonionic, they do not interfere with this binding.

Unbound reporter is then removed, using methods known in the art. Detergents may be added to the wash solution to dissociate non-specifically bound reporter, which may adsorb weakly to the solid surface of the reagent. Analyte-bound reporter is then detected via methods appropriate to the reporter group used.

D. Discovery Applications

The rapid binding reagent may be used for isolation of sequences related to, though not homologous with, known sequences. A typical example is in the cloning of a new gene which is suspected to be related to a known family of genes. In this case, unknown positions in the target sequence may be covered by degenerate bases, such as inosine, in the target specific probe. The rapid pairing reagent is able to rapidly bind nucleic acids in the sample and place them in very close proximity to target probes on the reagent, thus enabling binding under low stringency. The low amount of background interference inherent in the method facilitates such cloning procedures as well as amplification procedures (e.g., PCR) using motif primers.

EXAMPLES

The following examples illustrate but are not intended in any way to limit the invention.

Example 1

Evaluation of Binding of Polynucleotides by Weakly Basic Amines as a Function of pH Cellulose particles (Cellex 410, BioRad, Richmond, Calif.) were treated with an excess of CDI (1,1'-carbonyl diimidazole), washed thoroughly, and then treated with an excess of the amine to be tested, having the general formula $H_2N—R—R_N$ or $HCH_3N—R—R_N$. Denatured salmon sperm DNA in a pH 4.5 buffer was passed through a column containing the functionalized cellulose particles, whereupon most of the DNA was typically trapped on the column. The column was then washed with buffers of increasing pH in increments of 0.5, up to pH 9.0. Eluant fractions were scanned for $A_{260}$ to determine the quantity of DNA eluted. FIG. 3 shows representative curves for three amines, wherein $R_N$ is morpholine, imidazole, and 2-pyridine.

Example 2

Preparation of a Silica Particle Having an Oligoamine Capture Probe and a Morpholino Target-Specific Probe Amine-functionalized silica microparticles 1 (FIG. 4) were prepared by heating 4μ glass beads in neat trimethoxy (3-aminopropyl)silane at approximately 90° C. overnight. The resulting particles had approximately 1.5 nmol amine functionality per 1.0 g. Aminosilane-derivatized glass beads are also commercially available, e.g. from Polysciences, Inc.

Spacer groups were attached by first activating PEG 1450 (1.45 g, 1 mmol, Sigma Chemical Co., St. Louis, Mo.) with 324 mg (2 mmol) CDI in 2 ml NMP at 43° C. for 30 minutes. This solution was shaken with the above microparticles for 3 hours at 37° C., giving microparticles derivatized with carbamate-activated PEG chains 2. Unreacted amino groups were capped with CDI to give urea groups 3. The product was purified by repeated suspension, centrifugation, and removal of supernatant, using two portions of NMP and four portions of acetonitrile, and dried under vacuum.

Capture probe and target-specific probe are added in the desired molar ratio, typically 1:1 to 4:1. They may be added sequentially or, preferably, simultaneously. In the present example, a 5'-piperazino base-protected 25-mer morpholino oligomer (4) is used as the target-specific probe, and an oligoamine as the rapid capture probe. The oligoamine is attached by first adding, in a solvent such as NMP, an alternating serine/N-methylglycine copolymer, preferably having about 10–30 repeating serine/N-methylglycine subunits (i.e., where y in FIG. 4 is about 10 to 30). The N-terminus of the copolymer reacts with activated groups 2. The morpholino oligomer is preferably added concurrently, also reacting with activated groups 2, and the reaction is incubated for about 4 hours at 43° C. The serine hydroxyl groups and terminal carboxyl group of the peptide copolymer are then activated with CDI, followed by addition of an excess of the amine-terminated weakly basic amine, designated by $H_2N—R—R_N$, giving the final structure shown in FIG. 4. Finally, base protecting groups on the morpholino oligomer are removed by treatment with concentrated $NH_4OH$ in DMF.

Example 3

Sequence-Specific Capture of Poly-A RNA

A. Preparation of Poly A-Tailed Rabbit α-Globin and HIV-1 gag RNA Transcripts

An RNA transcript containing rabbit α-globin sequences was prepared. In vitro RNA transcription used T7 RNA polymerase (MegaScript™ RNA transcription kit, Ambion, Austin, Tex.) and a template designated pM7αL containing sequences from the rabbit α-globin gene. The pM7αL template was first linearized by digestion with the restriction endonuclease BsrG1, such that approximately 0.5 kb of sequence was available downstream of the promotor and before the cut site. Radiolabelled UTP ($\alpha$-$^{32}$P-UTP, Easy Tides, DuPont/NEN, No. Billerica, Mass.) was included in the transcription reactions at 140 μl per 20 μl reaction. Reactions were allowed to proceed for 5 to 6 hours at 37° C., after which unincorporated $\alpha$-$^{32}$P-UTP was removed using a ProbeQuant™ gel filtration column (Pharmacia, Piscataway, N.J.), followed by precipitation with one-half volume LiCl (Lithium Chloride Precipitating Solution, Ambion, Austin, Tex.) for 1 hour to overnight at −20° C. The precipitated RNA transcript was pelleted by a 15 minute centrifugation step at maximum speed in a microcentrifuge. To ensure complete removal of unincorporated radiolabelled UTP, the pellet was further rinsed with ice-cold 70% ethanol, briefly air-dried, then redissolved in a minimal volume of RNase-free $H_2O$. Assuming 50 μg of RNA as a reasonable yield from a 20 μl transcription reaction, resuspension in 10 μl of RNase-free $H_2O$ results in approximately 5 μg/μl RNA.

An RNA transcript containing HIV-1 sequences from the gag region was similarly prepared from a PCR product and tailed with poly A polymerase. A fragment of sequence contained in the plasmid pBENN7 was amplified using PCR with the primers 1308F (5'-GGA TCC TAA TAC GAC TCA CTA TAG GGA GGC ATT ATC AGA AGG AGC CAC CCC ACA AG, SEQ ID NO: 6, containing HIV-1 sequences as well as having the T7 RNA polymerase promoter, such that the amplicon can serve as a template for efficient RNA transcription) and 1793R (5'-GGT ACT GAT AGC TAG TTC TAG TGT AGC CGC TGG TCC CAA TGC T, SEQ ID NO: 7, containing sequences complementary to the HIV-1 genome in the gag region). These primers generate an approximately 528 bp PCT product, including the T7 promoter sequences.

A poly-A sequence was then added to the 3'-end of each RNA transcript using a non-template dependent RNA polymerase, poly A polymerase (Gibco/BRL, Ground Island, N.Y.; #18032-029; 1.6 U/ul) and cold ATP (Gibco/BRL; 18330-019). A tailing reaction mixture (150 µl), containing 40 mM Tris-HCl (pH 8.0 at room temperature), 10 mM $MgCl_2$, 2.5 mM $MnCl_2$, 150 mM NaCl, 0.5 mM Atp, 50 µg/ml acetylated bovine serum albumin, 2 mM dithiothreitol, 60 Units recombinant ribonuclease inhibitor (rRNasin, Promega Biotech, Madison, Wis.), approximately 37.5 µg of radiolabelled RNA transcript (prepared as above), and 30 Units poly A polymerase, was incubated at 37° C. 50 µl aliquots were removed after 30 minutes, 1 hour, and 2 hours of incubation. A one µl aliquot was then counted by Cherenkov counting in a liquid scintillation counter.

Approximately 500,000 cpm of each tailed RNA preparation was electrophoresed on a 4% polyacrylamide gel containing 7 M urea at 150 Volts, with cooling. Mobilities were compared with those of a commercially available RNA molecular size marker (RNA Century Marker, Ambion; #7780, with 100, 200, 300, 400, and 500 nt RNA's), a 628 nt transcript prepared by in vitro RNA transcription of an EcoRI digested pM7αL plasmid DNA, and the radiolabelled RNA transcript without poly A tailing. A significant mobility shift, compared with the untailed RNA, showed that poly A tailing was successful. Since the mobility of the tailed RNA's was less than that of the 628 nt marker transcript, it was judged that at least 100 A's had been added. Increasing tail lengths were observed as incubation time increased from 30 minutes to 2 hours.

B. Rapid Capture and Target-Specific Probes

Two morpholino oligomers were prepared as described in, e.g., U.S. Pat. No. 5,185,444. The analyte-targeted probe, designated Neu-Probe™ 124, had the sequence 5'-BIOTIN-GGU GGU UCC UUC UCA GUC GGA CUG G, (SEQ ID NO: 2), where the 5' designation refers to the orientation of the probe with respect to a complementary DNA or RNA sequence, to which it binds in an antiparallel orientation. The sequence is complementary to the α-globin RNA transcript prepared from pM7αL and tailed with poly A as described above.

The rapid capture probe, designated Neu-Probe™ 213, had the sequence 5'-BIOTIN-S-S-UUU UUU UUU UUU UUU UUU UUU UUU U SEQ ID NO: 1, where the 5' designation refers to the orientation of the probe with respect to a complementary DNA or RNA sequence, to which it binds in an antiparallel orientation, and where S—S refers to a disulfide bond capable of being cleaved by a reducing agent such as DTT. The probe is capable of base-pairing with a stretch of A residues, such as are found in eukaryotic mRNA's, some viral RNA's, and the poly A-tailed RNA transcripts prepared above.

C. Attachment of Probes to Magnetic Microparticles

Streptavidin-coated superparamagnetic particles (Dynabeads™ M-280, 2.8µ diameter, Dynal A. S., Oslo, Norway) were treated as recommended by the supplier, in order to render them RNase-free. Beads (6.5 mg) were washed sequentially with two 1 ml volumes of diethylpyrocarbonate (DEPC)-treated 0.1 N NaOH, 50 mM NaCl, and 1 ml of DEPC-treated 100 mM NaCl, followed by resuspension at 10 mg/ml in DEPC-treated 100 mM NaCl and storage at 4° C.

These RNase-free M-280 beads were prepared to contain either $U_{25}$ (Neu-Probe™ 213) alone, Neu-Probe™ 124 alone, or a combination of the two probes. Thus, 300 µl of M-280 beads at 10 mg/ml were washed once in 300 µl of Binding/washing Buffer (10 mM Tris-Cl, pH 7.5 at room temperature, 1 mM EDTA, 1 M NaCl, in DEPC-treated $H_2O$), then resuspended in 300 µl of the same buffer, for a final concentration of 10 mg/ml. To each of three aliquots of 200 µl M-280 beads (10 mg/ml) were added one of the following: (a) 90 µl of 20 µM Neu-Probe™ 124; (b) 90 µl of 20 µM $U_{25}$; or (c) 90 µl of a 1:1 mixture of 20 µM Neu-Probe™ 124 and 20 µM $U_{25}$. The reactions were incubated for 1 hour at room temperature, with frequent mixing, then washed 5 times with 300 µl Binding/Washing Buffer per wash, separating for 1 minute on a magnetic microparticle concentrator (MPC-E, Dynal) during each wash step. Each coated M-280 bead preparation was finally resuspended in 200 µl of Binding/Washing Buffer, for a final concentration (assuming quantitative recovery of microparticles) of approximately 10 mg/ml.

D. Sequence-Specific Capture of Poly-A Tailed α-Globin RNA

Radiolabelled and poly-A tailed RNA transcripts, prepared as in Section A above, were diluted in Capture Buffer (0.5 M LiCl, 0.5% lithium dodecyl sulfate, 100 mM Tris-Cl, pH 8.0 at room temperature) for approximately $10^4$ cpm/10 µl. This solution was estimated to be at a concentration of approximately 478 pM. M-280 beads were magnetically separated and resuspended in Capture Buffer prior to use. To 10 µl RNA transcripts diluted in Capture Buffer was added 5 µl of 10 mg/ml M-280 beads which had been treated with either Neu-Probe™ 124, $U_{25}$, the combination of the two probes, or no probes, as described above. Each RNA preparation was incubated with each of the following, for a total of 8 reactions:

1. M-280 beads containing the α-globin specific sequence (Neu-Probe™ 124 SEQ ID NO: 2) only;

2. M-280 beads containing the $U_{25}$ sequence only (Neu-Probe™ 213 SEQ ID NO: 1);

3. M-280 beads containing both Neu-Probe™ 124 and 213 (SEQ ID NOS: 1 and 2, respectively); and 4. M-280 beads containing no capture probe sequences, as a control for nonspecific sticking to the polystyrene microparticles.

The HIV-1 RNA was non-homologous to the sequence-specific probe used in this experiment and served as a control for non-specific capture. The α-globin RNA transcript contained sequences complementary to the sequence of Neu-Probe™ 124 SEQ ID NO: 2. Both transcripts were poly-A tailed, such that they could be captured by the $U_{25}$ Neu-Probe™ 213.

The RNA was allowed to incubate with the M-280 capture particles in a polypropylene microcentrifuge tube with gentle shaking at 37° C. for 30 minutes. Magnetic separation was then performed for 1 minute, and the supernatant was recovered for estimation of non-captured RNA. In order to ensure that no beads were taken into the supernatant fraction, only 10 µl was withdrawn, and care was taken to avoid contacting the pipet tip with the pellet of M-280 beads near the bottom of the microcentrifuge tube. The supernatant was maintained on ice for the duration of the experiment. This fraction was designated Supernatant.

To the bead pellet was then added 500 µl Capture Buffer, followed by vigorous resuspension and magnetic separation for 1 minute. The supernatant from this wash step was aspirated with a pipet tip and discarded. To the bead pellet was finally added 20 µl Release Buffer (Capture Buffer containing also 50 mM DTT). The beads were resuspended and allowed to incubated in the Release Buffer with gentle shaking at 37° C. for 1 hour. Magnetic separation was then performed for 1 minute, and 15 µl of the supernatant, designated as Pellet, was taken.

Supernatant and Pellet fractions were next mixed with Gel Loading Buffer and electrophoresed on 7% polyacrylamide gels containing 7 M urea, in IX TBE (Tris-borate-EDTA buffer). The poly-A tailed α-globin and HIV-1 RNA's were also loaded as mobility markers. The wet gels were wrapped in plastic wrap and exposed to X-ray film overnight (approximately 16 hours) at 4° C., with one intensifying screen.

Gel 1, containing the Supernatant fractions (i.e., the uncaptured RNA), provided an estimate of the relative amounts of RNA which were not captured in each of the 8 capture reactions. Only those M-280 preparations containing $U_{25}$ captured significant amounts of RNA transcripts, and resulted in efficient capture of both α-globin and HIV-1 sequences.

Gel 2, containing the Pellet fractions (i.e., the captured RNA), provided an estimate of the relative amounts of RNA which was captured, then released, from each of the 8 capture reactions. The α-globin sequences were efficiently released from beads containing $U_{25}$ (Neu-probe 213) only. Much less RNA was released from beads containing the α-globin specific sequence (Neu-Probe™ 124 SEQ ID NO: 2) in addition to the $U_{25}$. HIV-1 RNA, a control for non-specific capture of a nonhomologous sequence by the α-globin specific probe, was released from beads containing either $U_{25}$ only and from those containing the combination of Neu-Probe™ 124 SEQ ID NO: 2 and $U_{25}$. Significant signals were not seen for release from beads containing only Neu-Probe™ 124 or no probe, as Gel 1 showed no capture by these bead preparations under the conditions used in this experiment.

The autoradiograph, described above, showed sequence-specific capture of α-globin poly-A RNA by an α-globin specific capture probe SEQ ID NO: 2, but not of a poly-A HIV-1 RNA, which was nonhomologous to the specific capture sequence. The combination of sequence-specific probe and rapid capture component ($U_{25}$) resulted in significantly more efficient capture than the sequence-specific probe alone, and in sequence-specific purification of α-globin sequences from the mixture of α-globin and HIV-1 RNA transcripts.

Example 4

Sequence-Specific Capture of HIV-1 RNA: Sample Preparation for Subsequent Amplification A. Preparation of RNA Transcripts HIV-1 and α-globin RNA's were prepared and tailed with poly-A as described in Example 1. Initial experiments, with HIV-CP1, used the HIV-1 RNA transcript prepared as described in Example 1. Experiments with multiple specific capture probes used an approximately 700 nucleotide RNA prepared as described in Example 1, but using as the transcription template an amplicon generated using the PCR primers 797F (5'-GGA TCC TAA TAC GAC TCA CTA TAG GGA GGA GAG CGT CAG TAT TAA GCG GGG GAG AAT SEQ ID NO: 8, containing HIV-1 sequence as well as having the T7 RNA polymerase promoter, such that the amplicon can serve as a template for efficient RNA transcription) and 1509R (5'-TGT CAT CCA TCC TAT TTG TTC CTG AAG GGT ACT SEQ ID NO: 9, containing sequences complementary to the HIV-1 genome in the gag region).

B. Target-Specific Probes

An HIV-1 sequence-specific morpholino probe was prepared which was complementary to HIV-1 genomic (sense strand) RNA in the gag region. The probe was designed to bind to the target RNA upstream of the SK 462 primer sequence (5'-AGT TGG AGG ACA TCA AGC AGC CAT GCA AAT, SEQ ID NO: 10), which is outside the amplicon region amplified by the primers SK 462 and SK 431 (5'-TGC TAT GTC AGT TCC CCT TGG TTC TCT, SEQ ID NO: 11). The probe is thus suitable for sample preparation of HIV-1 RNA for subsequent amplification by PCR using these primers, as described in Section E, below. The probe was designated HIV-CP1 and was composed of the sequence as follows: 5'-BIOTIN-PEG3400-UUU AAA UCU UGU GGG GUG GCU CC (SEQ ID NO: 3), where the 5' designation refers to the orientation of the probe with respect to a complementary DNA or RNA sequence, to which it is bound in an antiparallel orientation. HIV-CP1 was synthesized with a 5'-biotin and a long spacer arm (polyethylene glycol, PEG-3400, Shearwater Polymers, Huntsville, Ala.) between biotin and the probe sequence.

Two additional probe sequences were prepared as follows:

HIV-CP2: 5'-biotin-PEG3400-GAA AAC AUG GGU AUC ACU UCU GGG C (SEQ ID NO: 4)

HIV-CP3: 5'-biotin-PEG3400-UGC GAA UCG UUC UAG CUC CCU G (SEQ ID NO: 5)

The quality of each oligo, following HPLC purification, was assessed by matrix-assisted laser desorption ionization mass spectroscopy (MALDI-TOF). Stock solutions (1 mM) in RNase-free water were stored at 4° C.

C. Attachment of Probes to M-280 Microparticles

Capture particles were prepared as described in Example 1, having HIV-CP1 (SEQ ID NO: 3) and $U_{25}$ (SEQ ID NO: 1) probes attached to the surface of streptavidin-coated microparticles (M-280, Dynal). Additional capture particles were prepared having all three HIV-specific capture probes described above, in addition to $U_{25}$.

D. Sequence-Specific Capture of HIV-1 RNA in Plasma Lysate, using Single Target Probe and Multiple Target Probes PureScript™ Cell Lysis Solution (Gentra Systems, Minneapolis, Minn.) was titrated to pH 7.5 with 10 N NaOH, in order to raise the pH into a range suitable for hybridization to occur. Lysates of normal human plasma (50 µl) were prepared by addition 3 volumes (150 µl) of the neutralized Cell Lysis Solution. After allowing the lysate to remain at least 5 minutes at room temperature, RNA ($10^4$ cpm) was added. A total of 4 reactions were prepared (see Table 1).

TABLE 1

| RNA | Capture Probe(s) |
| --- | --- |
| HIV-1 gag | (SEQ ID NO: 1) $U_{25}$ |
| rabbit α-globin | (SEQ ID NO: 1) $U_{25}$ |
| HIV-1 gag | (SEQ ID NOS: 1,3) $U_{25}$, HIV-CP1 |
| rabbit α-globin | $U_{25}$, HIV-CP1 |

100 μg of M-280 beads having the indicated capture probes were added, and each reaction was incubated at 37° C. with constant shaking for 30 minutes. Capture particles were magnetically separated (MPC-E, Dynal) and washed three times with 50 mM DTT. The amount of radioactivity associated with the beads was then determined in a liquid scintillation counter, and a percent recovery was calculated with reference to the cpm added to the capture reaction.

Initial experiments, with a single specific capture probe (SEQ ID NO: 3) and $U_{25}$, gave selective retention of HIV-1 RNA. These results demonstrate sequence-specific purification of HIV-1 sequences from the mixture of α-globin and HIV-1 RNA transcripts. Recovery of HIV-1 RNA was 37% in reaction 3; and <10% in reactions 1, 2, and 4. In separate experiments, with RNA bound to particles having only HIV-CP1, some loss was observed upon heating at 37° C. This suggested that higher recoveries could be obtained by using a longer capture probe, with higher $T_m$, or perhaps by using multiple capture probes.

Particles were subsequently prepared by coupling probes HIV-CP1, HIV-CP2, HIV-CP3, and $U_{25}$ (SEQ ID NOS: 3, 4, 5, and 1, respectively) to M-280 beads. Increased recovery was obtained (51.4%), suggesting that multiple capture probes facilitate retention of RNA on the particles.

E. PCR Amplification of Captured HIV-CP1 RNA

Particles treated with equimolar amounts of $U_{25}$ (SEQ ID NOS: 1 and 3, respectively) and HIV-CP1 probes, described above, were used to capture poly-A tailed HIV-1 RNA diluted to much lower concentrations than conventionally used in experiments with a scintillation counting endpoint. The captured RNA was amplified by RT-PCR using the primers SK 462 and 5'-biotin-SK 431, whose sequence is given in Section B, above. Because the HIV-CP1 probe was designed to bind outside of the amplicon region of the target RNA, PCR amplification could be carried out without releasing the bound RNA molecules.

Following 30 amplification cycles, PCR products were detected in a microplate hybridization format. The products were heat-denatured, and the probe SK 102, labelled with alkaline phosphatase, was hybridized in solution. Hybrids were captured in avidin-coated microwells, followed by detection using the fluorescent substrate 4-methylumbelliferyl phosphate. Results indicated that HIV-1 RNA at clinically relevant low copy number was capturable using the present method, and that the captured RNA was amplifiable by RT-PCR.

Example 5

Capture of poly-A RNA at High and Low Ionic Strength

Capture by a $dT_{25}$ polynucleotide (Dynal) and morpholino $U_{25}$ (Neu-Probe™ 213; see Example 1) was compared in high-salt (0.5 M LiCl, 0.5% lithium dodecyl sulfate, 100 mM Tris, pH 8.0, 10 mM EDTA) and low-salt (1 mM EDTA, pH 8.0) solutions. Radiolabelled poly-A tailed RNA, prepared as described in Example 1, was diluted to approximately $10^4$ cpm/10 μl, corresponding to approximately 0.5 to 5 nM. Beads containing either the $dT_{25}$ polynucleotide or the morpholino $U_{25}$ probe were washed three times in 1 mM EDTA, pH 8.0, to remove storage solution, and 50 μg were added to each sample. Following incubation at 37° C. with constant shaking, beads were magnetically separated. The supernatant was counted, and the fraction of RNA captured was calculated.

Results are shown in FIG. 6. Efficient capture was obtained within 1 minute in high-salt buffer for both probes. Morpholino $U_{25}$, in contrast to $dT_{25}$, was able to hybridize in low-salt buffer.

Example 6

RNA Isolation in the Presence of Polymerase Inhibitors

Plasma was spiked with high levels of heme (100 μg/50 μl) and heparin (20 μg/50 μl) and then extracted using one of several RNA isolation methods, each of which uses a different principle for purification: (a) extraction with acid guanidinium phenol (Tri Reagent™, Molecular Research Center, Cincinnati, Ohio); (b) salt precipitation (Gentra Systems, Minneapolis, Minn.); (c) silica binding (Qiagen™ HCV RNA); (d) extraction with a cationic detergent (Catrimox-14™, Iowa Biotech); and (e) hybridization-based capture with a morpholino $U_{25}$ probe (see Example 1). Extracts were spiked with HIV RNA corresponding to $10^4$ copies/reaction and assessed for inhibition in two separate PCR runs. Inhibition was thus assessed independently of RNA recovery.

As shown in FIG. 7, only hybridization-based purification avoids co-purification of either heme or heparin at these levels. All of the other schemes co-purified heparin, resulting in very low PCR yields, and several co-purified some level of heme.

While the invention has been described with reference to specific methods and embodiments, it will be appreciated that various modifications may be made without departing from the invention.

---

It is claimed:

1. A rapid pairing reagent for isolation or detection of a polynucleotide analyte molecule having a selected target base sequence, in a sample containing the analyte molecule and non-target polynucleotides, said reagent comprising
   a solid substrate,
   linked to said substrate, a capture component effective to non-selectively bind polynucleotide molecules, including said analyte molecule and non-target polynucleotides, in said sample, and
   also linked to said substrate, a target-specific probe effective to selectively bind said target base sequence of said analyte molecule to form a substrate-probe-target complex,
   wherein said capture component is effective to release said polynucleotide molecules under conditions which do not disrupt said substrate-probe-target complex.

2. The reagent of claim 1, wherein said capture component and said target-specific probe are linked to said substrate in a relative proximity effective to allow concomitant binding of said analyte molecule to said capture component and to said target-specific probe.

3. The reagent of claim 1, wherein said capture component comprises an amine having a pKa in the range of about 4.0 to about 8.0 and effective to bind polynucleotides at a pH below its pKa and to release polynucleotides at a pH substantially above its pKa.

4. The reagent of claim 3, wherein said amine is a polymeric amine.

5. The reagent of claim 1, wherein said capture component is linked to the substrate via a cleavable linkage, and said conditions are effective to cleave said linkage.

6. The reagent of claim 1, wherein said analyte molecule has a polyadenylated terminal sequence, and said capture component comprises a nucleic acid-binding polymer having a poly-uracil or poly-thymine sequence.

7. The reagent of claim 5, wherein said linkage is selected from the group consisting of a disulfide, a vicinal diol, an ortho-nitrobenzyl ester, an ester, a peptide, and an oligosaccharide.

8. The reagent of claim 1, wherein said target-specific probe is a polymeric moiety having a base sequence effective to specifically bind said target base sequence.

9. The reagent of claim 8, wherein said polymeric moiety is polyanionic and is selected from the group consisting of a polynucleotide and a polynucleotide analog.

10. The reagent of claim 8, wherein said polymeric moiety has a nonionic backbone and is selected from the group consisting of a morpholino oligomer and a peptide nucleic acid.

11. A method for isolation or detection of a polynucleotide analyte molecule having a selected target base sequence, in a polynucleotide-containing sample containing the analyte molecule and non-target polynucleotides, said method comprising
contacting said sample with a rapid pairing reagent, where said reagent comprises
a solid substrate,
linked to said substrate, a rapid capture component which non-selectively binds polynucleotide molecules, including said analyte molecule and non-target polynucleotides, in said sample,
and also linked to said substrate, a target-specific probe which binds selectively to said target base sequence of said analyte molecule to form a substrate-probe-target complex, and
exposing said rapid pairing reagent to conditions which release said polynucleotide molecules from said capture component without disrupting said substrate-probe-target complex, and
isolating or detecting said analyte molecule bound to said target-specific probe.

12. The method of claim 11, wherein said detecting comprises exposing said rapid pairing reagent to a detectable reporter group which binds to said analyte molecule, removing unbound reporter group, and examining said reagent for the presence of said reporter group.

13. The method of claim 12, wherein said target-specific probe has a nonionic backbone, and said reporter group is a cationic reporter which electrostatically binds said analyte molecule.

14. The method of claim 11 wherein said isolating comprises exposing said rapid pairing reagent to conditions which disrupt said substrate-probe-analyte complex.

15. The method of claim 14, wherein said disrupting conditions disrupt Watson-Crick base-pair hydrogen bonding between the probe and the analyte molecule.

16. The method of claim 14, wherein said probe is linked to said substrate via a cleavable substrate-probe linkage which is not cleavable under conditions effective to cleave the linkage of the capture component, and said disrupting conditions include treating with a reagent which cleaves said substrate-probe linkage.

17. The method of claim 11, for solid phase enzymatic amplification of a portion of said analyte molecule, further comprising exposing the rapid pairing reagent to amplification reagents, said reagents comprising polynucleotide primers, deoxynucleoside triphosphates, and a nucleic acid polymerase, wherein said analyte molecule has an amplicon region which lies outside of said target base sequence.

18. A method for isolation or detection of a polynucleotide analyte molecule having a selected target base sequence, in a polynucleotide-containing sample containing the analyte molecule and non-target polynucleotides, said method comprising
contacting said sample with a first substrate having linked thereto a rapid capture component which non-selectively binds polynucleotide molecules, including said analyte molecule and non-target polynucleotides, in said sample,
removing said substrate from said sample; and
releasing said polynucleotide molecules from said substrate such that they contact a selective binding reagent, wherein said selective binding reagent comprises a second substrate having linked thereto a target-specific probe which binds selectively to said target base sequence of said analyte molecule to form a substrate-probe-target complex,
and wherein said releasing comprises exposing said first substrate to conditions which release said molecules from said capture component without interfering with the formation of said substrate-probe-target complex, and
isolating or detecting said analyte molecule.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:

(A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:1:

UUUUUUUUUU UUUUUUUUUU UUUUU                                     25

(2) INFORMATION FOR SEQ ID NO:2:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:2:

GGUGGUUCCU UCUCAGUCGG ACUGG                                     25

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:3:

UUUAAAUCUU GUGGGGUGGC UCC                                       23

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:4:

GAAAACAUGG GUAUCACUUC UGGGC                                     25

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:5:

UGCGAAUCGU UCUAGCUCCC UG                                        22

(2) INFORMATION FOR SEQ ID NO:6:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (xi) SEQUENCE DESCRIPTION: SEQ ID NO:6:

GGATCCTAAT ACGACTCACT ATAGGGAGGC ATTATCAGAA GGAGCCACCC CACAAG   56

```
(2) INFORMATION FOR SEQ ID NO:7:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO:7:

GGTACTGATA GCTAGTTCTA GTGTAGCCGC TGGTCCCAAT GCT                         43

(2) INFORMATION FOR SEQ ID NO:8:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (xi) SEQUENCE DESCRIPTION: SEQ ID NO:8:

GGATCCTAAT ACGACTCACT ATAGGGAGGA GAGCGTCAGT ATTAAGCGGG GGAGAAT         57

(2) INFORMATION FOR SEQ ID NO:9:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:9:

TGTCATCCAT CCTATTTGTT CCTGAAGGGT ACT                                   33

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:10:

AGTTGGAGGA CATCAAGCAG CCATGCAAAT                                       30

(2) INFORMATION FOR SEQ ID NO:11:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:11:

TGCTATGTCA GTTCCCCTTG GTTCTCT                                          27
```